United States Patent
Li

(10) Patent No.: US 10,071,137 B2
(45) Date of Patent: Sep. 11, 2018

(54) METHOD FOR DECREASING MORTALITY ASSOCIATED WITH CHRONIC LIVER DISEASE BY USE OF LONG-ACTING HUMAN RECOMBINANT SOLUBLE TUMOR NECROSIS FACTOR α RECEPTOR

(71) Applicant: Zhenyi Li, Shanghai (CN)

(72) Inventor: Hai Li, Shanghai (CN)

(73) Assignee: Zhenyi Li, Shanghai (CN)

( * ) Notice: Subject to any disclaimer, the term of this patent is extended or adjusted under 35 U.S.C. 154(b) by 0 days.

(21) Appl. No.: 15/372,011

(22) Filed: Dec. 7, 2016

(65) Prior Publication Data

US 2017/0106049 A1    Apr. 20, 2017

Related U.S. Application Data

(63) Continuation of application No. 14/821,311, filed on Aug. 7, 2015, now abandoned, which is a continuation of application No. PCT/CN2013/071497, filed on Feb. 7, 2013.

(51) Int. Cl.
*A61K 38/17*    (2006.01)
*A61K 9/127*    (2006.01)
*A61K 47/48*    (2006.01)

(52) U.S. Cl.
CPC ........ *A61K 38/1793* (2013.01); *A61K 9/1271* (2013.01); *A61K 47/48215* (2013.01)

(58) Field of Classification Search
CPC .............. A61K 38/1793; A61K 9/1271; A61K 47/48215
See application file for complete search history.

(56) References Cited

U.S. PATENT DOCUMENTS

2003/0148955 A1    8/2003    Pluenneke

FOREIGN PATENT DOCUMENTS

CN          1951496        4/2007

OTHER PUBLICATIONS

Boetticher NC, et al. (Dec. 2008). Gastroenterology. 135(6):1953-60. (doi: 10.1053/j.gastro.2008.08.057).*
Nam H-S, et al: Yonsei Med. J. 50(4):569-575. Aug. 31, 2009. Available online at doi: 10.3349/ymj.2009.50.4.569.
Alkermes Licenses Technology Platform for Long-Acting Fusion Proteins from Acceleron Pharma—www.acceleronpharma.com./releasedetail.cfm?ReleaseID=785721. Dec. 3, 2009. Retrived from the internet Aug. 30, 2016.
International Search Report of PCT/CN2013/071497, dated Nov. 21, 2013, and English language translation therof, 10 pages total.
Chen et al., "The expression of apoptosis by TNF-alpha, TNFR, and Bcl-2 family in chronic liver disease," Journal of Clinical Hepatology, 2002, vol. 18, No. 6, pp. 342-343, English language abstract provided and cited in International Search Report of PCT/CN2013/071497.
Chen et al., "Expressions of TNF-alpha, TNFR, and Bcl-2 family in liver tissue of chronic liver disease," Medical Journal of National Defending Forces in North China, 2002, vol. 14, No. 4, pp. 229-231, English language abstract provided and cited in International Search Report of PCT/CN2013/071497.
Supplementary European Search Report issued in corresponding European Application No. 13874779.5 dated Jul. 29, 2016 (8 pages).
Gao et al.: "241 Continuously blocking tumor necrosis factor-alpha signal transduction prevent acute of acute-on-chronic liver failure mice from death effectively"; Journal of Hepatology, vol. 56, 2012, 1 page, cited in Supplementary European Search Report issued in European Application No. 13874779.5 dated Jul. 29, 2016, and in Chinese Office Action issued in corresponding Chinese Application No. 201380072579.6 dated May 19, 2017 and Chinese Office Action issued in corresponding Chinese Application No. 201380072579.6 dated Nov. 28, 2017, full article.
Mutchnick et al.: "Thymosin treatment of chronic hepatitis B: a placebo-controlled pilot trial"; Hepathology, vol. 14, No. 3, 1991, 1 page, abstract provided, cited in Supplementary European Search Report issued in European Application No. 13874779.5 dated Jul. 29, 2016.
Liu et al.: "PP-158 Effect of Xuebijing injection in patients of liver cirrhosis with spontaneous bacterial peritonitis", International Journal of Infectious diseases, International Society for Infectious diseases, vol. 14, 2010, 1 page, abstract provided, cited in Supplementary European Search Report issued in European Application No. 13874779.5 dated Jul. 29, 2016.
Etsuro Hatano: "Tumor necrosis factor signaling in hepatocyte apoptosis"; Journal of Gastroenterology and Hepatology, vol. 22, 2007, 1 page, abstract provided, cited in Supplementary European Search Report issued in European Application No. 13874779.5 dated Jul. 29, 2016.
Zhao et al.: "Intrahepatic expression of TNF-α and CD68+ cells in patients with acute-on-chronic hepatitis B liver failure"; J Clin Hepatol, 2009, vol. 12, pp. 31-34, full article provided, cited in Chinese Office Action issued in corresponding Chinese Application No. 201380072579.6 dated Jul. 6, 2016.

* cited by examiner

*Primary Examiner* — Robert S Landsman
(74) *Attorney, Agent, or Firm* — Hamre, Schumann, Mueller & Larson, P.C.

(57)    ABSTRACT

The proposed invention involves the use of new drugs with the recombinant soluble tumor necrosis α receptor (Hus-TNFR) and belongs to the gene engineering technology and gene function application field. This invention uses type I or type II long-acting HusTNFR (LHusTNFR) to perform an intervention for severe liver injury in rats with chronic liver disease using 5 types of animal models. The results showed that LHusTNFR, which has a half-life of 12-140 hours, shows excellent efficacy for preventing the development of severe liver injury on chronic liver disease and for treating early-stage severe liver injury on chronic liver disease. It also significantly reduced the mortality of the model animals. Its efficacy for the prevention and treatment of early-stage severe liver injury on chronic liver disease was significantly better than that of non-LHusTNFR.

4 Claims, 5 Drawing Sheets
Specification includes a Sequence Listing.

METHOD FOR DECREASING MORTALITY ASSOCIATED WITH CHRONIC LIVER DISEASE BY USE OF LONG-ACTING HUMAN RECOMBINANT SOLUBLE TUMOR NECROSIS FACTOR α RECEPTOR

TECHNOLOGY FIELD

This invention, which involves the use of new drugs that include the recombinant soluble tumor necrosis α receptor (HusTNFR), belongs to the gene engineering technology and gene function application field. This invention specifically involves the prevention and treatment of severe liver injury on chronic liver disease by long-acting HusTNFR (LHusTNFR).

TECHNOLOGY BACKGROUND

Severe liver injury on chronic liver disease (also called chronic liver disease with severe liver injury) refers to patients with underlying chronic liver diseases who have recently suffered one or more major injuries in the liver, thus causing severe liver injury induced by acute and massive hepatocyte necrosis, which can involve important extrahepatic organs and cause multiple organ failure, including liver failure. This disease has a very high short-term mortality (40-80%) and is a severe liver disease that threatens the lives of patients. The characteristics of chronic liver disease with severe liver injury are the following: 1) the presence of chronic underlying liver disease. Chronic underlying liver disease refers to chronic hepatitis, liver fibrosis or cirrhosis induced by a variety of causes. Specific underlying liver diseases include hepatitis virus-induced chronic hepatitis, liver fibrosis or cirrhosis, chronic alcoholic liver disease, non-alcoholic fatty liver disease, autoimmune liver disease, or drug-induced liver injury. 2) There are relatively clear and acute hepatic injury causes, including intestinal endotoxins, taking liver injury medications, alcoholism, hepatitis virus mutations, recurrence of the original hepatitis virus, infection with a new hepatitis virus, or chemical injury. 3) There is rapid deterioration of liver function within a short-term period (disease duration usually within 4 weeks), which can develop into multiple organ failure. 4) The 3-month mortality rate is greater than 40-80%.

Clinically, liver injury and severe liver injury are classified as different liver diseases. First, the pathogenesis of these 2 diseases is different. The development of acute hepatic necrosis is the key pathogenic characteristic of severe liver injury, and massive/submassive hepatic necrosis is the characteristic pathological change in liver tissues during this disease. However, liver injury involves only mild hepatic inflammation and necrosis, and there is no massive/submassive hepatic necrosis in its pathology. This is the key feature distinguishing liver injury from severe liver injury. Next, the disease outcomes differ. Liver injury will not develop into single organ or multiple organ failure and will not result in death, whereas severe liver injury patients usually progress to multiple organ failure and have a mortality rate of 40-80%. Furthermore, the clinical treatment results differ significantly. In clinical practice, many drugs can effectively prevent and treat general liver injury. For example, it has been reported that the conventional TNFα receptor with a short half-life can effectively treat or prevent liver injury; however, this agent is essentially ineffective for severe liver injury. Currently, there are no chemicals, biotech drugs, or natural drugs that can effectively prevent or treat severe liver injury on chronic liver disease. These are the fundamental reasons for the high mortality rate of this group of diseases and the short-term mortality rate of approximately 40-80%.

According to the presence of underlying liver diseases before the development of the disease, severe liver injury is divided into acute severe liver injury and severe liver injury on chronic liver disease. Severe liver injury that occurs in a healthy liver is called acute severe liver injury (also known as acute liver failure) whereas acute liver injury that occurs during chronic liver disease is called severe liver injury on chronic liver disease (also known as acute-on-chronic liver failure).

Acute severe liver injury occurs in healthy livers. After acute and massive hepatocyte necrosis, healthy livers have a very strong regenerative ability. With the help of anti-hepatic necrosis drugs, liver cells can rapidly regenerate to restore the liver function to the lowest level necessary for the basic requirements of body operation, thus improving the mortality rate. Severe liver injury on chronic liver disease occurs in livers with chronic hepatitis, fibrosis, or cirrhosis. Livers with chronic lesions are more susceptible to acute hepatocyte necrosis after liver injury than are healthy livers. In addition, because of local blood circulation disorders in liver tissues and the poor quality of residual liver cells caused by underlying diseases, livers with chronic liver disease cannot rapidly regenerate after acute and massive hepatic necrosis; thus, the diseased liver cannot bear the basic operational demands of the body within a short time period, resulting in patient death.

Therefore, significant liver degeneration defects and being prone to acute hepatic necrosis are two important differences between severe liver injury on chronic liver disease and acute severe liver injury; consequently, they are classified as two different groups of diseases in clinical situations. They have different diagnostic and therapeutic methods. In addition, drugs that are effective for acute severe liver injury are ineffective for severe liver injury on chronic liver disease.

The conventional soluble TNFα receptor can relieve liver injury caused by mild hepatocyte necrosis to some extent. However, it cannot effectively reduce acute severe liver injury or severe liver injury on chronic liver disease caused by large areas of hepatocyte necrosis. In addition, researchers in this field still cannot understand the reason for the unsatisfactory results. Therefore, it is currently difficult to practically apply the soluble TNFα receptor in the clinical treatment of severe liver injury.

In summary, there is an urgent need to identify why the TNFα receptor shows poor efficacy for the treatment of severe liver injury on chronic liver disease to further improve TNFα receptor treatment and to use this agent to effectively and rapidly prevent the development of severe liver injury on chronic liver disease. Therefore, the TNFα receptor can become an excellent drug for the prevention and treatment of severe liver injury on chronic liver disease (acute-on-chronic liver failure) in clinical situations.

INVENTION DISCLOSURE

The first aspect of the invention involves the use of LHusTNFR in the preparation of drugs for preventing and/or treating severe liver injury on chronic liver disease or hepatocyte necrosis based on chronic liver diseases.

In another preferred embodiment, the mentioned treatment is the treatment of the early-stage severe liver injury on chronic liver disease and the early-stage hepatic necrosis related disease based on chronic liver disease.

In another preferred embodiment, the mentioned early-stage severe liver injury on chronic liver disease refers to the severe liver injury on chronic diseases with the status of SIRS.

In another preferred embodiment, the mentioned SIRS refers to the increase of peripheral blood pro-inflammatory cytokines TNFα and IL-6 or the increase of the pro-inflammatory cytokines TNFα and IL-6 and the anti-inflammatory cytokine IL-10 together.

In another preferred embodiment, the mentioned LHus-TNFR has a half-life of 12-140 hours.

In another preferred embodiment, the mentioned LHus-TNFR is selected from:
  a. a fusion protein between human type I tumor necrosis factor α receptor and the human IgG1:Fc fragment,
  b. a fusion protein between human type II tumor necrosis factor α receptor and the human IgG1:Fc fragment,
  c. a conjugated product between the amino terminus of human type I tumor necrosis factor α receptor and PEG,
  d. a conjugated product between the carboxyl terminus of human type I tumor necrosis factor α receptor and PEG,
  e. a conjugated protein between the amino terminus of human type II tumor necrosis factor α receptor and PEG,
  f. a conjugated product between the carboxyl terminus of human type II tumor necrosis factor α receptor and PEG,
  h. a human type I tumor necrosis factor α receptor protein product embedded in a PEG-liposome mixture, or
  i. a human type II tumor necrosis factor α receptor protein product embedded in a PEG-liposome mixture.

In another preferred embodiment, the mentioned LHus-TNFR can significantly reduce the mortality rate of animals with severe liver injury on chronic liver disease;
  Prevent the massive/submassive necrosis of liver tissues;
  Decrease caspase 3 activity levels by 70-80%;
  Decrease the TUNEL-positive cell count/high power field in liver pathology by more than 80%;
  Decrease the liver tissue injury score by 40-70%;
  Essentially eliminate the pathological characteristics of massive/submassive hepatic necrosis;
  Decrease the level of NF-κB in the liver by 30-50%;
  Decrease the peak values of TNFα, IL-6, and IL-10 in the peripheral blood by 40-95%;
  Decrease the peak values of TNFα and IL-6 in the liver by 40-80%; and/or
  Increase the IL-22 and IL-22 receptors in the liver by 2- to 5-fold.

In another preferred embodiment, the mentioned LHus-TNFR can significantly decrease the mortality rate of animals with early-stage severe liver injury on chronic liver disease;
  Prevent the massive/submassive necrosis of liver tissues;
  Decrease caspase 3 activity levels by 70-80%;
  Decrease the TUNEL-positive cell count/high power field in liver pathology by more than 80%;
  Decrease the liver tissue injury score by 40-70%;
  Essentially eliminate the pathological characteristics of massive/submassive hepatic necrosis;
  Decrease NF-κB levels in the liver by 30-50%;
  Decrease the peak values of TNFα, IL-6, and IL-10 in the peripheral blood by 40-95%;
  Decrease the peak values of TNFα and IL-6 in the liver by 40-80%; and/or
  Increase the IL-22 and IL-22 receptors in the liver by 2- to 5-fold.

In other preferred embodiment, chronic liver disease with severe liver injury (also known as severe liver injury on chronic liver disease) refers to diseases that occur in the presence of chronic liver diseases and that are caused by viruses, immune injury, toxins (or drugs), alcohol, or a high-fat diet; this class of liver diseases occurs as a result of the rapid deterioration of liver functions caused by a recently suffered major blow to the liver that induces acute and massive liver cell necrosis that can develop into multiple organ failure with a short-term mortality rate greater than 20%.

In another preferred embodiment, the mentioned chronic liver diseases with severe liver injury include the following: severe alcoholic hepatitis, hepatitis virus associated hepatitis, acute-on-chronic liver failure caused by liver fibrosis or cirrhosis, severe liver injury caused by nonalcoholic fatty liver disease, severe liver injury caused by autoimmune liver disease, and drug-induced severe liver injury caused by chronic liver disease.

In another embodiment, the mentioned hepatic necrosis refers to acute and large area hepatic necrosis (massive/submassive hepatic necrosis), which is one of the characteristic manifestations in liver pathology.

The second aspect of the invention provides a pharmacological composition wherein the said pharmacological composition contains the following:
  (i) an effective amount of LHusTNFR selected from the following groups:
    a. a fusion protein between human type I tumor necrosis factor α receptor and the human IgG1:Fc fragment,
    b. a fusion protein between human type II tumor necrosis factor α receptor and the human IgG1:Fc fragment,
    c. a conjugated product between the amino terminus of human type I tumor necrosis factor α receptor and PEG,
    d. a conjugated product between the carboxyl terminus of human type I tumor necrosis factor α receptor and PEG,
    e. a conjugated protein between the amino terminus of human type II tumor necrosis factor α receptor and PEG,
    f. a conjugated product between the carboxyl terminus of human type II tumor necrosis factor α receptor and PEG,
    h. a human type I tumor necrosis factor α receptor protein product embedded in the PEG-liposome mixture, or
    i. a human type II tumor necrosis factor α receptor protein product embedded in the PEG-liposome mixture,
  and
  (ii) pharmacologically acceptable carriers.

In another preferred embodiment, the mentioned pharmacological composition also contains an effective amount of one or more drugs selected from the drugs listed below:
  (iii) α-thymosin, human hepatocyte growth factor (huHGF), glutathione, matrine, human serum albumin, polyene phosphatidylcholine, a variety of coenzyme vitamins, and Xuebijing (traditional Chinese medicine).

The third aspect of the invention provides a method for the prevention of severe liver injury on chronic liver disease and hepatocyte necrosis on the basis of chronic liver diseases; thus, people who require treatment are given LHus-TNFR.

The fourth aspect of this invention provides a method for the treatment of early-stage severe liver injury on chronic liver disease and early-stage hepatocyte necrosis on the basis of chronic liver diseases; thus, people who require treatment are given LHusTNFR.

In another embodiment, the mentioned LHusTNFR is selected from the following group:
  a. a fusion protein between human type I tumor necrosis factor α receptor and the human IgG1:Fc fragment,
  b. a fusion protein between human type II tumor necrosis factor α receptor and the human IgG1:Fc fragment, c. a conjugated product between the amino terminus of human type I tumor necrosis factor α receptor and PEG, d. a conjugated product between the carboxyl terminus of human type I tumor necrosis factor α receptor and PEG, e. a conjugated protein between the amino terminus of human type II tumor necrosis factor α receptor and PEG, f. a conjugated product between the carboxyl terminus of human type I tumor necrosis factor α receptor and PEG, h. a human type I tumor necrosis factor α receptor protein product embedded in a PEG-liposome mixture, or i. a human type II tumor necrosis factor α receptor protein product embedded in a PEG-liposome mixture.

Accordingly, this invention provides TNFα that can effectively and rapidly prevent the development of severe liver injury on chronic liver disease; therefore, it can be an excellent drug for the prevention and treatment of severe liver injury on chronic liver disease (acute-on-chronic liver failure) in clinical situations.

DESCRIPTION OF FIGURES

FIG. 2A shows the dynamic changes of the peripheral blood pro-inflammatory cytokines (TNFα and IL-6) and the anti-inflammatory cytokine (IL-10).

FIG. 2B shows the dynamic changes of the liver tissue pro-inflammatory cytokines (TNFα and IL-6) and the anti-inflammatory cytokine (IL-10). The solid line is the control group receiving normal saline treatment. The dotted line is the prevention group that was treated with the long-acting type II receptor (type II HusTNFR-IgG1:Fc) through the subcutaneous injection route.

FIG. 4A shows the dynamic changes of the peripheral blood pro-inflammatory cytokines (TNFα and IL-6) and the anti-inflammatory cytokine (IL-10).

FIG. 4B shows the dynamic changes of the liver tissue pro-inflammatory cytokines (TNFα and IL-6) and the anti-inflammatory cytokine (IL-10). The solid line is the control group receiving normal saline treatment. The dotted line is the prevention group that was treated with the long-acting type II receptor (type II HusTNFR-IgG1:Fc) through the intravenous route.

EMBODIMENTS

Figure 1:
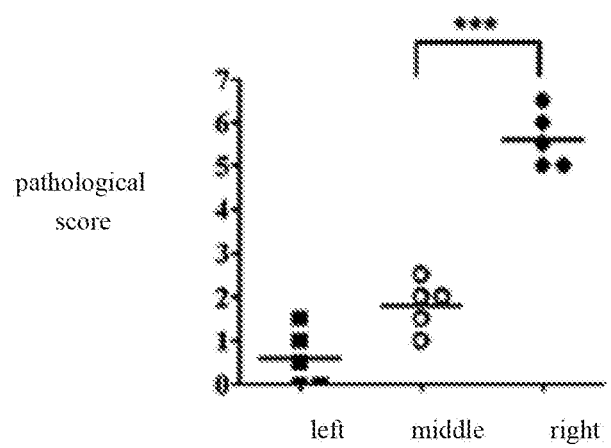
FIG. 1 shows the liver injury pathological scores in model 1 of embodiment 4. The left column is the liver with chronic liver fibrosis. The middle column is the long-acting type II receptor subcutaneous injection prevention group, and the right column is the control group.

After long-term and extensive studies and testing, inventors for the first time showed that the prevention and treatment of larger area acute hepatocyte necrosis requires the persistent and stable inhibitory function of soluble TNFα receptors. Therefore, inventors modified TNFα receptors through a variety of methods to prepare one group of long-acting soluble TNFα receptors that can maintain stable and persistent treatment functions in the blood and liver of the body, which can effectively prolong the action time of soluble TNFα receptors as an active component in the body. For chronic liver diseases with severe liver injury, inventors greatly increased the efficacy of TNFα for chronic liver disease. Therefore, for the first time, the modified TNFα receptors can be applied to large-area/massive hepatic necrosis-induced chronic liver disease with severe liver injury on chronic liver disease. Thus, this invention was completed accordingly.

Studying these inventions showed that the new use of LHusTNFR results in the excellent prevention and treatment of severe liver injury on chronic liver disease. This invention showed that LHusTNFR, which is formed by different protein structures and has an excellent efficacy for the prevention and treatment of chronic liver disease with severe liver injury in different types of model animals through embodiments.

As used herein, "long-acting soluble tumor necrosis factor α receptor" refers to tumor necrosis factor α receptor with an extended half-life (i.e., it can last for a longer time in the body at an effective concentration). Generally, the half-life of "long-acting soluble tumor necrosis factor α receptor" is greater than 12 hours (e.g., 12-140 hours). The half-life of tumor necrosis factor α receptor can be extended by a variety of methods, which include but are not limited to manipulating the connection between tumor necrosis factor α receptor and the human IgG1:Fc fragment, the connection between tumor necrosis factor α receptor and PEG, and embedding tumor necrosis factor α receptor in the PEG-liposome mixture. The preferred "long-acting soluble tumor necrosis factor α receptor" is the "long-acting human recombinant soluble tumor necrosis factor α receptor".

The purpose of this invention was to provide new medical uses of the recombinant soluble tumor necrosis factor α receptor gene (HusTNFR), particularly new uses for the prevention of chronic liver disease with severe liver injury and the treatment of early-stage chronic liver disease with severe liver injury using long-acting human recombinant tumor necrosis factor α receptor (LHusTNFR), which is formed by the HusTNFR gene or the modified HusTNFR protein.

An additional purpose of this invention was to provide a drug to further greatly reduce the mortality of chronic liver disease with severe liver injury compared to the conventional soluble tumor necrosis factor α receptor. It can increase the clinical treatment efficacy mainly through the extension of the half-life of the soluble TNFα receptor to prolong the action time of the drugs.

This invention used LHusTNFR to perform an intervention on rats with severe liver injury on chronic liver disease in severe liver injury on chronic liver disease animal models. The results showed that the mortality rates of the intervention group and the model group were 0 and 60-90%, respectively.

The mentioned tumor necrosis factor (TNF) is the recombinant long-acting soluble protein that results from the binding between TNFα and the corresponding cell membrane receptor, including the long-acting human soluble type I tumor necrosis factor α receptor (LHusTNFRI) and the long-acting human recombinant soluble type II tumor necrosis factor α receptor (LHusTNFRII). Their half-life is extended more than 10-fold compared to that of the general human recombinant soluble type I (HusTNFRI) and type II (HusTNFRII) tumor necrosis factor α receptors. Their forms of presence are (1) a connection between the carboxyl terminus of HusTNFRI or HusTNFRII and the human immunoglobulin IgG:Fc fragment, (2) a connection between the amino terminus or carboxyl terminus of HusTNFRI or HusTNFRII with PEG, or (3) HusTNFRI or HusTNFRII embedded in a PEG-liposome. LHusTNFRI and LHusTNFRII have significantly preferable efficacies in the prevention and treatment of chronic liver disease with severe liver injury compared to that of HusTNFRI or HusTNFRII.

Animal models of severe liver injury on chronic liver diseases use the following procedure: 1) After being sensitized by heterologous serum albumin, the tail vein was repeated injected for 6 weeks to induce chronic liver injury and liver fibrosis. The model was established by the intradermal injection of D-galactosamine and endotoxin. 2) After the liver cirrhosis model was established through repeated subcutaneous injections of a small dose of carbon tetrachloride for 8 weeks, the model was established by the intradermal injection of D-galactosamine and endotoxin. 3) After the chronic alcoholic liver injury and liver fibrosis model was established by feeding the rats low concentrations of alcohol for 12 weeks, the model was established by the intradermal injection of D-galactosamine and endotoxin. 4) After the non-alcoholic fatty liver disease model was established by feeding the rats a high-fat diet for 12 weeks, the model was established by the intradermal injection of D-galactosamine and endotoxin. The mortality rate of the above acute injuries on chronic animals due to liver failure ranged from 60-100%. The above models were at the SIRS stage after 0-2 hours of D-galactosamine and endotoxin attacks (TNFα, IL-6, and IL-10 significantly increased) and at the non-SIRS stage after 2-24 hours (TNFα, IL-6, and IL-10 returned to their levels before disease development).

To compare the efficacy of LHusTNFR on chronic liver disease with severe liver injury at different disease stages, this invention established a chronic liver disease with severe liver injury animal model in which CARS was induced by ConA several times, followed by a GaIN/LPS strike.

The LHusTNFR in this invention was constructed through
  a. a fusion protein between human type I tumor necrosis factor α receptor and the human IgG1:Fc fragment,
  b. a fusion protein between human type II tumor necrosis factor α receptor and the human IgG1:Fc fragment,
  c. a conjugated product between the amino terminus of human type I tumor necrosis factor α receptor and PEG,
  d. a conjugated product between the carboxyl terminus of human type I tumor necrosis factor α receptor and PEG,
  e. a conjugated protein between the amino terminus of human type II tumor necrosis factor α receptor and PEG,
  f. a conjugated product between the carboxyl terminus of human type II tumor necrosis factor α receptor and PEG,
  h. a human type I tumor necrosis factor α receptor protein product embedded in a PEG-liposome mixture, or
  i. a human type II tumor necrosis factor α receptor protein product embedded in a PEG-liposome mixture.

LHusTNFR was prepared for the prevention and treatment steps. 1) After being sensitized by heterologous serum albumin, the tail vein was repeatedly injected for 6 weeks to induce chronic liver injury and liver fibrosis. The model was established by the intradermal injection of D-galactosamine and endotoxin. 2) After the liver cirrhosis model was established through repeated subcutaneous injections of a small dose of carbon tetrachloride for 8 weeks, the model was established by the intradermal injection of D-galactosamine and endotoxin. 3) After the chronic alcoholic liver injury and liver fibrosis model was established by feeding the rats low concentrations of alcohol for 12 weeks, the model was established by the intradermal injection of D-galactosamine and endotoxin. 4) After the non-alcoholic fatty liver disease model was established by feeding the rats a high-fat diet for 12 weeks, the model was established by the intradermal injection of D-galactosamine and endotoxin. The results showed that type I or type II LHusTNFR with a long half-life has an excellent efficacy for the prevention and treatment of chronic liver disease with severe liver injury in model animals and can significantly reduce the mortality of the model animals. The results indicated that LHusTNFR has prevention and treatment value and can be further prepared as a drug to greatly reduce the mortality of chronic liver disease with severe liver injury.

In this invention, the following procedure was used: (1) For SEQ ID NO: 1, the method for the preparation of type I LHusTNFR included the preferential recombination of the gene encoding the type I sTNFR (human) outer membrane amino acids (positions 1-171 of SEQ ID NO: 1) and the gene encoding the human immunoglobulin γ1 chain Fc fragment (IgG1:Fc) (positions 172-403 of SEQ ID NO: 1) with related plasmids. DNA restriction endonuclease was used to identify and screen for positive clones that carried the type I TNFR-IgG1:Fc fusion fragment. Nucleotide sequencing was used to validate whether the gene was correct. Between the gene encoding the type I sTNFR (human) outer membrane amino acids (positions 1-171 of SEQ ID NO: 1) and the gene encoding the amino acids of the human immunoglobulin γ1 chain Fc fragment (IgG1:Fc) (positions 172-403 of SEQ ID NO: 1), 0-6 nucleotides encoding amino acids G(n)S could be added as a linker fragment.

(2) For SEQ ID NO: 2, the method for the preparation of the type II LHusTNFR gene included the recombination of the gene encoding the type II sTNFR (human) outer membrane amino acids (positions 1-235 of SEQ ID NO: 2) and the gene encoding the human immunoglobulin γ1 chain Fc fragment (IgG1:Fc) amino acids (positions 236-467 of SEQ ID NO: 2) with related plasmids. DNA restriction endonuclease was used to identify and screen for positive clones that carried the type II TNFR-IgG1:Fc fusion fragment. Nucleotide sequencing was used to validate whether the gene was correct.

The above type I and type II TNFR-IgG1:Fc cDNA fragments were recombined with expression vectors to construct the recombinant expressing plasmids. This invention was not limited to specific expression plasmids. In the preferred embodiment, prokaryote expression plasmids were used. The above recombinant plasmids can be introduced into proper host cells using conventional methods. This invention is not limited to any specific host cell as long as it can express the said recombinant expression plasmids. In the preferred embodiment, this invention used mammalian cells, such as CHO cells.

All the operations in molecular biology are carried out according to "Molecular cloning: a laboratory manual" (Sambrook and D. W. Russell, New York: Cold Spring Harbor Laboratory Press).

(3) The cDNA encoding the extra-membrane amino acids of sTNFR (human) type I (i.e., amino acids 1-171 of SEQ ID NO: 1) is cloned into a expression vector to produce a recombinant expression plasmid (SEQ ID NO: 3)

The present invention is not limited to any specific expression plasmids. In a preferred embodiment, a prokaryotic expression vector, for example, pET28, is used.

The said recombinant expression vector may be introduced into an appropriate host cells as previously taught. The present invention is not limited to any specific host cells. Any host cells, as long as it allows the expression of the recombinant expression vectors can be used. In a preferred embodiment, E. coli BL21 is employed. The expression product according to the present invention is secreted as inclusion bodies in the cytoplasm of the host cells. The inclusion bodies may be isolated from the lysate of the host cells, and then lysed with high concentration of urea or guanidine hydrochloride. The LHusTNFR type I is purified from the lysate of the inclusion bodies, and then renatured to give the active LHusTNFR type I.

Active mPEG(s) of molecular weight (MW) no less than 20,000 may be coupled to the amino terminal or the carboxyl terminal of HusTNFR type I. The present invention is not limited to any specific mPEG molecules. In a preferred embodiment, mPEG2-ALD of MW 40,000 from Shearwater corporation (New Jersey, USA) was coupled to the amino terminal of HusTNFR type I. And, in another embodiment, an mPEG2-NHS easter of MW 40,000 from Shearwater corporation (New Jersey, USA) was coupled to the carboxyl terminal of HusTNFR type I.

The reaction can be expressed by the formula:

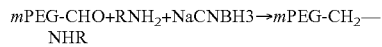
mPEG-CHO+RNH$_2$+NaCNBH3→mPEG-CH$_2$—NHR

The reaction condition includes pH 7.9 and a duration of 12 hrs.

(4) The cDNA encoding the extra-membrane amino acids 1-235 of sTNFR (human) type II is cloned into an expression vector to produce a recombinant expression plasmid (SEQ ID NO: 4).

The present invention is not limited to any specific expression plasmids. In a preferred embodiment, a prokaryotic expression vector, for example, pET28, was used.

The said recombinant expression vector may be introduced into an appropriate host cells as previously taught. The present invention is not limited to any specific host cells. Any host cells, as long as it allows the expression of the recombinant expression vectors can be used. In a preferred embodiment, E. coli BL21 was used. The expression product according to the present invention is secreted as inclusion bodies into the cytoplasm of host cells. The inclusion bodies may be isolated from the lysate of the host cells, and then lysed with high concentration of urea or guanidine hydrochloride. The LHusTNFR type II is purified from the lysate of the inclusion bodies, and then renatured to give the active LHusTNFR type II.

Active mPEG(s) with a molecular weight (MW) of no less than 20,000 may be coupled to the amino or the carboxyl terminal of HusTNFR type II. The present invention is not limited to any specific mPEG molecules. In a preferred embodiment, mPEG2-ALD of MW 40,000 from Shearwater corporation (New Jersey, USA) was coupled to the amino terminal of HusTNFR type II. And in another embodiment, an mPEG2-NHS easter of MW 40,000 (Shearwater corporation, New Jersey, USA) was coupled to the carboxyl terminal of HusTNFR type II.

The reaction may be expressed by the formula:

mPEG-CHO+RNH2+NaCNBH3--?mPEG-CH2-NHR

The reaction condition includes pH 7.9 and a duration of 12 hrs.

(5) The HusTNFR type I or the HusTNFR type II is encapsulated with the long circulating liposome-polyethylene glycol-derived phospholipid to produce the long-acting HusTNFR type I or type II.

DOPE-PEG-MAL (WM 4108.04) is produced by reacting dioleoyl-phosphatidylethanolamine (DOPE)(WM 744.04, Aanti Polar Lipids, U.S.A.), NHS-PEG3540-MAL (Nhydroxysulfosuccinimide-polyoxyethylene (MW 3540)-maleimide) (MW 3477, Aanti Polar Lipids, U.S.A.) and TEA in a molar ratio of 1:1:0.1 in the presence of triethylamine as the catalyst at 25° C. for 6 hrs and then subjecting the resultant to centrifugation, evaporation and vacuum dehydration.

Then, the long circulating liposome-polyethylene glycol-derived phospholipid is produced by reacting the obtained DOPE-PEG-MAL, EPC (L-α-Phosphatidylcholine, MW 760.09, cholesterol (MW 386.67), and mPEG-2000-DOPE (MW 2801.51) (Aanti Polar Lipids, U.S.A.) at a molar ratio of 200:20:10:1 in chloroform in a water bath at 40° C., and then rotary evaporating at 100-150 r/min to remove the organic solvents, adding PBS (PH 7.4) to allow complete hydration at room temperature, extruding repeatedly with Mini Extruder, and passing through 100 nm filter for 15 times.

Finally, the long-acting HusTNFR type I or type II is obtained by adding HusTNFR type I (SEQ ID NO:3) or HusTNFR type II (SEQ ID NO:4) in PBS to the PBS solution of the obtained long circulating liposome-polyethylene glycol-derived phospholipid, oscillating at 4° C. for 30 min, and passing through CL-4B (Pharmacia, USA) to remove encapsulated HusTNFR type I or HusTNFR type II.

As can be measured, half-life of the HusTNFR-IgG type I: and type II:Fc fusion proteins are maintained at effective levels in vivo was from 40 to 100 hrs. The half-life of both PEG-HusTNFR and the HusTNFR encapsulated within the long circulating liposome-polyethylene glycol-derived phospholipid was from 3 to 5.5 days separately.

It can be seen that all the LHusTNFRs produced in different forms according to methods described above each have a half-life more than 12 hours (from 12 to 140 hours). The In contrast, the normal soluble tumor necrosis factor α receptor has a half-life of only 50 minutes to 2 hours.

This invention uses genetic engineering methods to produce LHusTNFR. The obtained product is highly efficient for the prevention and treatment of chronic liver disease with severe liver injury. Compared to that of the conventional HusTNFR properties, the half-life of LHusTNFR significantly extended, the efficacy for the prevention and treatment of chronic liver disease with severe liver injury and reduced the mortality.

This invention revealed that LHusTNFR can effectively prevent and treat model animals with severe liver injury on chronic liver disease and can significantly reduce the mortality rate of these diseases. That is, the different types of LHusTNFR can reduce the mortality rate of animals with different mechanisms of severe liver injury on chronic liver disease from 60-90% to 0%. Although many reported studies have shown that some chemicals, biotech drugs, or natural medicines could reduce the mortality rate of chronic liver disease with severe liver injury to some extent through a variety of mechanisms (reduced from 40-80% to 30-50%), there are no reports in this field showing that a drug can reduce the high mortality rate of chronic liver disease with severe liver injury from 60-90% to 0%.

This invention reveals that the mechanisms underlying the significant reduction of the mortality rate of disease model animals by LHusTNFR include the prevention of hepatocyte apoptosis, the protection of hepatocyte survival, and the promotion of hepatocyte regeneration. Our study further elucidated that the prevention and treatment of chronic liver disease with severe liver injury by LHusTNFR requires the combined functions of the following two mechanisms: 1) a reduction in the production of liver apoptosis signals by blocking TNFα signal transduction to exert the function for anti-acute hepatocyte necrosis and 2) an increase in the expression of the IL-22 and IL-2 receptors to increase the survival and regeneration ability of hepatocytes (some literature has previously reported that IL-22 has the ability to promote hepatocyte regeneration and increase hepatocyte survival).

Therefore, this invention reveals that, in addition to blocking acute hepatocyte apoptosis/necrosis, the effective prevention and treatment of chronic liver disease with severe liver injury also requires the promotion of hepatocyte survival and regeneration. However, for acute severe liver injury, effective treatment only requires the blocking of acute hepatocyte apoptosis/necrosis. This invention elucidates that after the prevention/treatment of animals with severe liver injury on chronic liver disease by LHusTNFR, the severity of hepatocyte apoptosis is significantly relieved, and the IL-22 signal that can protect hepatocytes and promote hepatocyte regeneration also increases to effectively treat this disease and significantly reduce the mortality rate.

This invention also innovatively shows that LHusTNFR has a different efficacy on animals at different stages of severe liver injury on chronic liver disease. It can significantly reduce the mortality of animals at the early stage of the disease; however, it cannot reduce mortality at the advanced and late stages of the disease.

According to the development of the immune status of the disease, chronic liver disease with severe liver injury is divided into three stages: early-systemic inflammatory response syndrome (SIRS), advanced-diminished SIRS stage, and late-compensatory anti-inflammatory response syndrome (CARS). Examining the studies showed that LHusTNFR (including TNFRII-IgG:Fc) can significantly reduce SIRS at the early stage of chronic liver disease with severe liver injury in rats. The immunological presentation of SIRS involves an increase in peripheral blood TNFα and IL-6 levels (increase of pro-inflammatory factors) or an increase in blood TNFα, IL-6, and IL-10 levels simultaneously (increase in pro-inflammatory and anti-inflammatory factors together) at the early stage of chronic liver disease with severe liver injury. In animal experiments, the researchers also showed that LHusTNFR (including TNFRII-IgG:Fc) cannot reduce the mortality rate of rats with severe liver injury on chronic liver disease in the presence of CARS. This result is similar to clinical reports showing that the mortality rate of patients with refractory acute alcoholic hepatitis was not reduced after treatment with TNFRII-IgG:Fc (Entarcept; brand name: Enbrel). In the above literature, late-stage or glucocorticoid treatment-ineffective patients were enrolled in the study. These patients were usually at the CARS stage; therefore, the immune system presentations included immune suppression characteristics such as a significant decrease of HLA-DR expression in monocytes, an increase in the peripheral blood anti-inflammatory factor IL-10, and no increase in the pro-inflammatory factors TNFα and IFNγ.

The four types of chronic liver disease with severe liver injury animal models that were used in this invention revealed that SIRS occurs 0-2 hours after the induction of severe liver injury by acute liver injury. For severe liver injury that occurs within 0-2 hours, the administration of LHusTNFR can reduce the mortality from 60-90% to 0%. Two hours after the development of severe liver injury, animals that had already passed the SIRS stage were administered LHusTNFR; however, the results showed that there was no efficacy in terms of a significant reduction of the mortality rate. Therefore, this invention identified that LHusTNFR has different treatment effects on the early stage (the presence of SIRS) compared to the middle and late stages (non-SIRS or CARS stage) of chronic liver disease with severe liver injury and explains why the efficacy for animals with severe liver injury on chronic liver disease at the CARS stage is poor. In addition, it also indicated that LHusTNFR has a significant efficacy for animals with early-stage chronic liver disease with severe liver injury at the SIRS stage and can greatly reduce the mortality rate. This invention also showed that preventive use of LHusTNFR can prevent the development of chronic liver disease with severe liver injury through blocking massive acute hepatocyte necrosis and inhibiting the occurrence of SIRS.

The four animal models of chronic liver disease with severe liver injury selected in this invention represent but are not limited to model animals that have chronic liver injury, liver fibrosis, or liver cirrhosis that is induced by ethanol (alcohol), a high-fat diet, immune injury, or chemical toxins that are attacked by endotoxin or viral nucleic acid to show the characteristics of chronic liver disease with severe liver injury such as acute hepatocyte necrosis, liver inflammation, rapid deterioration of liver functions, and high mortality within a short time period.

This invention also provides a pharmacological composition for treating hepatocyte necrosis or chronic liver disease with severe liver injury. It contains the aforementioned LHusTNFR and pharmacologically acceptable carriers. Usually, these substances can be prepared in non-toxic, inert, and pharmacologically acceptable aqueous carrier media. The pH is generally approximately 5-8, and the preferred pH is approximately 6-8; however, pH values can be changed as a result of the properties of the prepared substances and diseases to be treated. The prepared pharmacological composition can be administered through conventional routes including (but not limited to) intraperitoneal, intravenous, or local administration.

The pharmacological composition in this invention can be directly used in the treatment of hepatocyte necrosis or chronic liver disease with severe liver injury. In addition, it can also be used with other related treatment agents. This group of treatment agents includes but is not limited to the following: α-thymosin, human hepatocyte growth factor (huHGF), glutathione, matrine, human serum albumin, polyene phosphatidylcholine, a variety of coenzyme vitamins, and Xuebijing (traditional Chinese medicine).

The pharmacological composition in this invention contains a safe and effective amount of the aforementioned LHusTNFR and pharmacologically acceptable carriers or excipients. These carriers include (but are not limited to) saline, buffer solution, glucose, water, glycerol, ethanol, and their combinations. Pharmacological preparations should match the drug administration method. The pharmacological composition in this invention can be prepared in an injection form. For example, it can be prepared with normal saline or a water solution with glucose or other adjuvants using conventional methods. Pharmacological compositions, such as injections or solutions, should be prepared under sterile conditions. The drug dosage of the active components is the effective treatment dose, for example, approximately 0.1 μg/kg body weight to 5 mg/kg body weight daily.

When using the pharmacological composition, the safe and effective dose of LHusTNFR in the formulation is administered to mammals. The safe and effective dose is usually at least 1 μg/kg body weight, and in most cases, it is no more than 8 μg/kg body weight. The preferred dose is between 10 µg/kg body weight and 1 mg/kg body weight. The specific dose should also consider factors such as the administration routes and health conditions of the patient, considerations that are within the skill range of experienced physicians.

Combined with the following specific embodiments, this invention is further elucidated. It should be understood that these embodiments are merely used to explain this invention; they are not intended to limit the scope of the invention. The specific conditions of the experimental methods are not described in the following embodiments. Generally, the conventional conditions are those described in "Molecular Cloning: A Laboratory Manual" (Joseph Sambrook and David W. Russell, New York: Cold Spring Laboratory Press) or conditions suggested by the manufacturers.

Embodiment 1

Methods for Establishing the 4 Types of Chronic Liver Disease with Severe Liver Injury Animal Models Model 1. A chronic liver disease with severe liver injury rat model was established by heterologous serum albumin sensitization and repeated injection to induce chronic liver injury/liver fibrosis, followed by the injection of D-galactosamine (GaIN) and endotoxin (lipopolysaccharide, LPS); this process was completed in 3 stages.

a. Heterologous albumin sensitization: female Wistar rats with a body weight from 120-150 g were used.

Human serum albumin was diluted with normal saline and emulsified with an equal amount of incomplete Freund's adjuvant. Multiple-point subcutaneous injections were performed on each rat at a dose of 0.5 ml (containing 4 mg of albumin) in each injection for a total of 4 treatments. The interval between the first and second injection was 14 days, and the interval between the third and fourth injection was 10 days. Ten days after the last immunization, blood was collected for antibody detection. Rats with positive antibodies were selected for subsequent experiments.

b. Chronic liver injury and liver fibrosis: albumin was injected into the tail vein twice a week. The first injection was at a dosage of 2.5 mg/animal. Subsequently, each challenge increased the dosage by 0.5 mg until reaching 4.5 mg. This dosage was maintained until week 6. The immune liver injury and liver fibrosis model was thus established. At this stage, the liver pathology of the animals showed (1) the hyperplasia of reticular fibers and collagen fibers in the portal area, which extend outwards. In addition, they occurred around the central vein, were distributed and scattered along the liver sinusoids, and were connected to one another. Lobules were wrapped with connective tissues, and some animals exhibited a pseudolobule formation; (2) lymphocyte, monocyte, and eosinophil infiltration occurred around the portal area and the central vein. The cellulose-like death of the lobular artery and inflammatory cell infiltration around the central vein could be observed. The immunofluorescence results showed that the portal area, hepatic sinusoid, and vessel wall all had immune complex deposition. Electron microscopy showed the transformation of stellate cells into myofibroblasts, which were distributed in the portal area. The surroundings had a large amount of collagen deposition. The deposited collagen formed a wider separation.

c. Acute challenge of D-GaIN/LPS in the above fibrotic rats: tail vein injections of albumin were conducted twice a week for a total of 6 weeks to induce liver fibrosis in the rats, followed by the intraperitoneal injection of 400 mg/kg of D-GaIN plus 100 µg/kg of LPS. The mortality rate of the rats in the model group after 24 h was 80-90%, and the mean survival time was approximately 16 hours. Four hours after the D-GaIN plus LPS injection, alanine aminotransferase began to increase, and the peak value was reached at 8-12 hours. Total bilirubin continuously increased 4 hours after the injection until the death of the animals. The plasma TNFα levels significantly increased 0.5 hours after the D-GaIN plus LPS injection, reached a peak at 1 hour, decreased at 2 hours, and resumed normal levels at 4 hours. Plasma IL-6 significantly increased at 0.5 hours, reached a peak at 2 hours, decreased at 3 hours, and returned to normal levels at 8 hours. The plasma IL-10 levels significantly increased at 0.5 hours, reached a peak at 1 hour, decreased at 2 hours, and resumed normal levels at 4 hours. Gross liver specimens showed severe congestion and swelling of the liver. The liver pathology showed focal or patchy necrosis in the regenerative nodules after 4 hours combined with a leukocyte reaction, scattered apoptotic bodies, and mild edema in the portal area. After 8 hours, hepatocyte necrotic loci in the nodules increased or showed a patchy fusion, and increases in red blood cells and the hyperplasia of interstitial cells and biliary epithelia were observed. After 12 hours, the hepatocytes in the majority of the regenerative nodules showed massive or submassive necrosis. Sinus dilation, red blood cell filling, Kupffer cell activation, and cytoplasm enlargement could be observed. There was microvesicular fatty degeneration and vacuolar degeneration in the residual hepatocytes, and the fibrous septa were completely retained. After 4 hours, electron microscopy showed a small amount of lipid droplets that were broken or had disappeared into the mitochondrial cristae. The hepatocytes showed a decrease of microvilli and early apoptotic presentation such as shrinkage and irregularly shaped nuclei. After 8 hours, the apoptotic cells significantly increased, and detached apoptotic bodies were observed. The extended foot processes of the activated Kupffer cells were in contact with hepatocytes or engulfed apoptotic bodies.

Model 2. Repeated subcutaneous injections of a small dose of carbon tetrachloride were performed for 8 weeks to establish the liver cirrhosis model. D-GaIN/LPS was then injected to establish the chronic liver disease with severe liver injury mode. It was completed in 2 stages.

a. The induction of liver cirrhosis in rats using carbon tetrachloride: subcutaneous injections of a small dose of carbon tetrachloride were performed using the common method reported in the literature for 8 weeks. The liver pathological results confirmed the presence of the cirrhosis liver specific pseudolobule structure.

b. The acute D-GaIN/LPS challenge was conducted in the above liver cirrhosis rats: an intraperitoneal injection of 400 mg/kg of D-GaIN plus 100 µg/kg of LPS was performed. The mortality rate of the rats in the model group after 24 hours was 80-90%, and the mean survival time was approximately 16 hours. Four hours after the injection of D-GaIN plus LPS, alanine aminotransferase began to increase, and the peak value was reached at 8-12 hours. The total bilirubin increased 4 hours after the injection and continuously increased until the death of the animal. The plasma TNFα levels significantly increased after 8 hours, and the IL-10 levels increased over time. The pathological results showed massive and submassive necrosis in the liver combined with the presence of cirrhosis pseudolobule, sinus dilation, red blood cell filling, activation of Kupffer cells, and cytoplasm enlargement. There was microvesicular fatty degeneration and vacuolar degeneration in the residual hepatocytes, and the fibrous septa were completely retained. After 4 hours, electron microscopy showed a small amount of lipid droplets that were broken or had disappeared into the mitochondrial cristae. The hepatocytes showed a decrease of microvilli and early apoptotic presentation such as shrinkage and irregularly shaped nuclei. After 8 hours, the apoptotic cells significantly increased, and detached apoptotic bodies were observed. The extended foot processes of the activated Kupffer cells were in contact with hepatocytes or engulfed the apoptotic bodies.

Model 3. The rats were fed low concentrations of ethanol for 12 weeks to establish the alcoholic chronic liver injury and liver fibrosis model. An intradermal injection of D-GaIN/LPS was then performed to establish the chronic liver disease with severe liver injury model. It was completed in 2 stages.

a. Alcoholic liver disease rats were induced by low concentrations of ethanol: the rats were fed with 10% ethanol mixed with a high-fat diet for 3-4 months. The pathological results confirmed the development of hepatic steatosis and liver fibrosis.

b. The acute D-GaIN/LPS challenge was conducted in the above liver cirrhosis rats: an intraperitoneal injection of 400 mg/kg of D-GaIN plus 100 μg/kg of LPS was performed. The mortality rate of the rats in the model group after 24 hours was 80-90%, and the mean survival time was approximately 16 hours. Four hours after the injection of D-GaIN plus LPS, alanine aminotransferase began to increase and peaked at 8-12 hours. The total bilirubin increased 4 hours after injection and continuously increased until animal death. The plasma TNFα levels significantly increased after 8 hours, and the IL-10 levels increased over time. The pathological results showed massive and submassive necrosis in the liver, sinus dilation, red blood cell filling, activation of Kupffer cells, and enlargement of the cytoplasm. There was microvesicular fatty degeneration and vacuolar degeneration in the hepatocytes, and the fibrous septa were completely retained. After 4 hours, electron microscopy showed a small amount of lipid droplets that were broken or had disappeared into the mitochondrial cristae. The hepatocytes showed a decrease of microvilli and early apoptotic presentations such as shrinkage and irregularly shaped nuclei. After 8 hours, the apoptotic cells significantly increased, and detached apoptotic bodies were observed. The extended foot processes by the activated Kupffer cells were in contact with hepatocytes or engulfed the apoptotic bodies.

Model 4. The rats were fed with a high-fat diet for 12 weeks to establish the non-alcoholic fatty liver model. D-GaIN/LPS was then injected to establish the chronic liver disease with severe liver injury model.

a. Non-alcoholic fatty liver rats were induced by a high-fat and high-sugar diet: the rats were fed with the common high-fat mixed with high-sugar diet for 3-4 months. The pathological results confirmed the development of hepatic steatosis, steatohepatitis, and partial liver fibrosis.

b. The acute D-GaIN/LPS challenge was performed in the above liver cirrhosis rats: an intraperitoneal injection of 400 mg/kg of D-GaIN plus 100 μg/kg of LPS was performed. The mortality rate of the rats in the model group after 24 hours was 80-90%, and the mean survival time was approximately 16 hours. Four hours after the injection of D-GaIN plus LPS, alanine aminotransferase began to increase, and the peak value was reached at 8-12 hours. The total bilirubin increased 4 hours after injection and continuously increased until animal death. The plasma TNFα levels significantly increased after 8 hours, and the IL-10 levels increased over time. The pathological results showed massive and submassive necrosis in the liver, sinus dilation, red blood cell filling, activation of Kupffer cells, and high levels of cytoplasm. There was microvesicular fatty degeneration and vacuolar degeneration in the hepatocytes, and the fibrous septa were completely retained. After 4 hours, electron microscopy showed a small amount of lipid droplets that were broken or had disappeared into the mitochondrial cristae. The hepatocytes showed a decrease of microvilli and early apoptotic presentation such as shrinkage and irregularly shaped nuclei. After 8 hours, the apoptotic cells significantly increased, and detached apoptotic bodies were observed. The extended foot processes of the activated Kupffer cells were in contact with the hepatocytes or engulfed the apoptotic bodies.

Embodiment 2

After the Induction of CARS by Multiple ConA Stimulations, the GaIN/LPS Challenge was Administered to Establish the Chronic Liver Disease with Severe Liver Injury Mouse Model A subcutaneous injection of a small dose of ConA was performed every 48 hours for a total of 3-5 times. The detection of peripheral blood showed that IL-10 significantly increased, whereas TNFα and IFNγ did not increase, which reflected the CARS immune status model. After challenge with a large dose of GaIN/LPS for 24 hours, the mortality rate of the animals was 15-20%. Liver pathology showed submassive necrosis in a smaller range with the simultaneous presence of local and patchy necrosis.

Embodiment 3

A Comparison of the Different Efficacies of NAC (N-Acetylcysteine) in the Prevention and Treatment of Drug-Induced Severe Liver Injury and Chronic Liver Disease with Severe Liver Injury The drug-induced acute severe liver injury rat model was established using the dose of acetaminophen that is commonly used in the literature. The short term mortality rate was approximately 40%. According to step a of model 2 in embodiment 1, the hepatic cirrhosis rat model was established using carbon tetrachloride. In addition, an equal dose of acetaminophen was used to establish the animal model of chronic liver disease with severe liver injury, which has a short term mortality of 40-60%. Six hours before the acetaminophen administration, an intravenous injection of NAC was administered to healthy rats to establish the prevention of chronic liver disease with severe liver injury by the NAC model. Six hours before the acetaminophen administration, an intravenous injection of NAC was performed in liver cirrhosis rats to establish the prevention of chronic liver disease with severe liver injury. After the administration of acetaminophen for 0.5 hours, an equal dose of NAC was given to the healthy and liver cirrhosis rats to treat the acute severe liver injury model and the chronic liver disease with severe liver injury model by NAC, respectively.

For the acute severe liver injury model, the NAC prevention group and the treatment group observed a reduction in the mortality of the model to 10-15%, whereas the mortality rate of chronic liver disease with severe liver injury induced by acetaminophen animals prevented and treated by NAC was 40-60%; this latter value did not differ from that in the control group. These results indicated that NAC cannot effectively reduce the mortality rate of animals with chronic liver disease with severe liver injury induced by acetaminophen.

The results showed that NAC is effective for the survival of acute severe liver injury that occurs in healthy livers but is not effective for animals with chronic liver disease with severe liver injury on the basis of liver cirrhosis.

Embodiment 4

Experiments of the Prevention of Chronic Liver Disease with Severe Liver Injury in Rats Using a Subcutaneous Injection of Long-Acting Recombinant Type II TNFα Receptor (Type II LHusTNFR) Represented by Type II HusTNFR-IgG1:Fc The subcutaneous injection of type II LHusTNFR (the type II LHusTNFR-IgG1:Fc prepared in method (2) is the preventative drug) into the above four types of chronic liver disease with severe liver injury models was evaluated before the acute challenge of D-GaIN/LPS at a dose of 5-50 mg/kg. In one preferred embodiment, the dose used in the invention was 12.5 mg/kg. This treatment group was named the long-acting type II receptor subcutaneous injection prevention group. The injection of the long-acting type II soluble receptor type II LHusTNFR-IgG1:Fc is not limited to a specific time before the acute challenge of D-GaIN/LPS as long as the administration of drugs occurs before the acute challenge of D-GaIN/LPS. The preferred time is 0 to 36 hours before the acute challenge of D-GaIN/LPS. In addition, conventional HusTNFR subcutaneous injection rats are prepared at a dose of 12.5 mg/kg, which is the conventional type II receptor prevention group. The control group was the same species of rats with a subcutaneous injection of an equal volume of normal saline. In the rats with immune liver fibrosis induced by heterologous albumin, liver cirrhosis induced by carbon tetrachloride, alcoholic liver disease induced by ethanol, and non-alcoholic liver disease induced by a high-fat diet, the mortality rate of rats in the long-acting type II TNFα receptor subcutaneous injection group 24 hours after the D-GaIN/LPS injection was 0, whereas the mortality rate in the conventional type II TNFα receptor prevention group was 66%. The mortality rate of the chronic liver disease with severe liver injury model control group that did not receive long-acting or conventional type II TNFα treatment (abbreviated as the "control group") was 90%. Gross pathology showed that the original features of chronic liver injury, liver fibrosis, and liver cirrhosis in the liver of the long-acting type II receptor prevention group were still retained; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group (p<0.01). Using model 1 as an example, the liver injury scores are shown in FIG. 1. The left column is the liver with chronic liver fibrosis, the middle column is the long-acting type II receptor subcutaneous injection prevention group, and the right column is the control group.

Figure 2A:
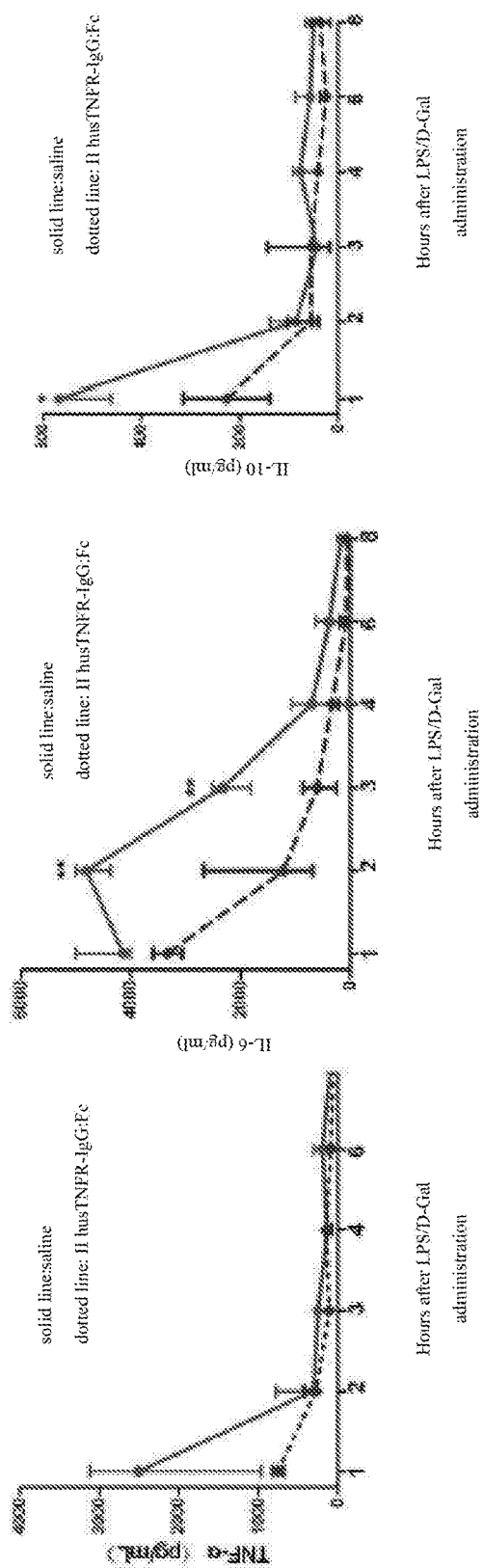
FIG. 2A and FIG. 2B, respectively, show the dynamic changes of the peripheral blood and liver tissue pro-inflammatory cytokines and anti-inflammatory cytokines after the LPS/D-GalN challenge in model 1 of embodiment 4.
Figure 2B:
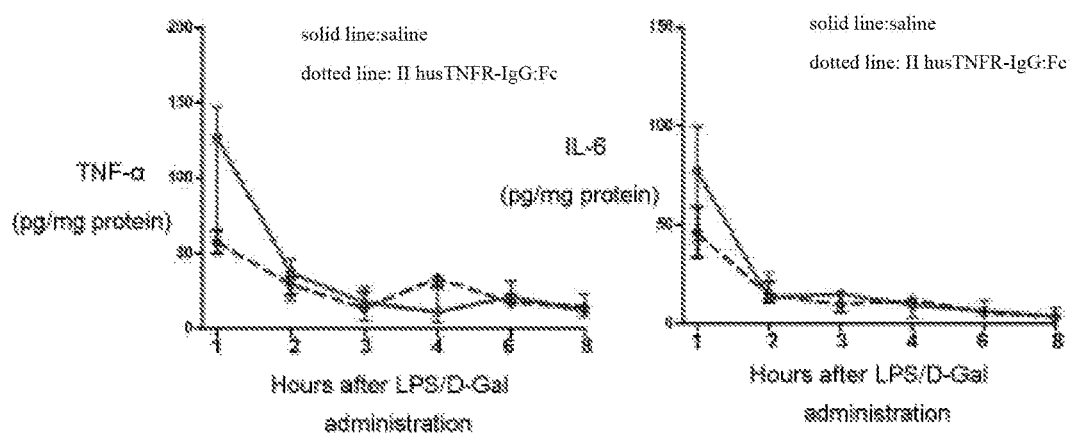
Figure 3:
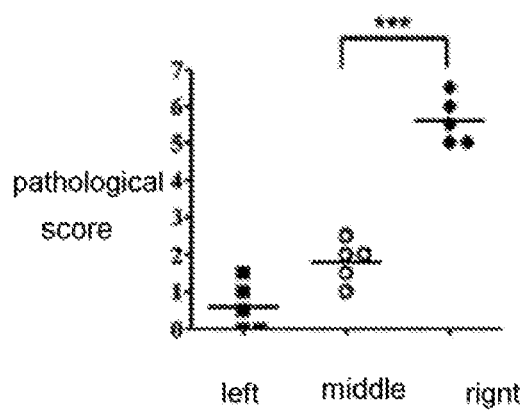
FIG. 3 shows the liver injury pathological scores in model 1 of embodiment 5. The left column is the liver with chronic liver fibrosis. The middle column is the prevention group receiving the long-acting type II receptor through the intravenous route. The right column is the control group.
Figure 4A:
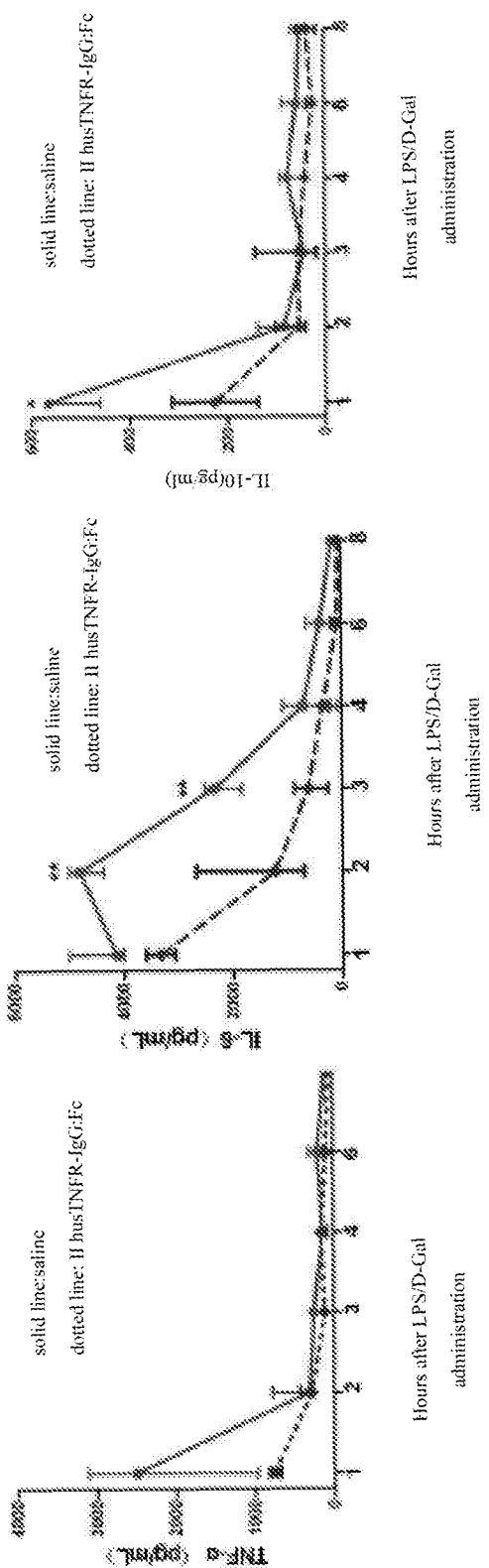
FIG. 4A and FIG. 4B, respectively, show the dynamic changes of the peripheral blood and liver tissue pro-inflammatory cytokines and anti-inflammatory cytokines after the LPS/D-GalN challenge in model 1 of embodiment 5.
Figure 4B:
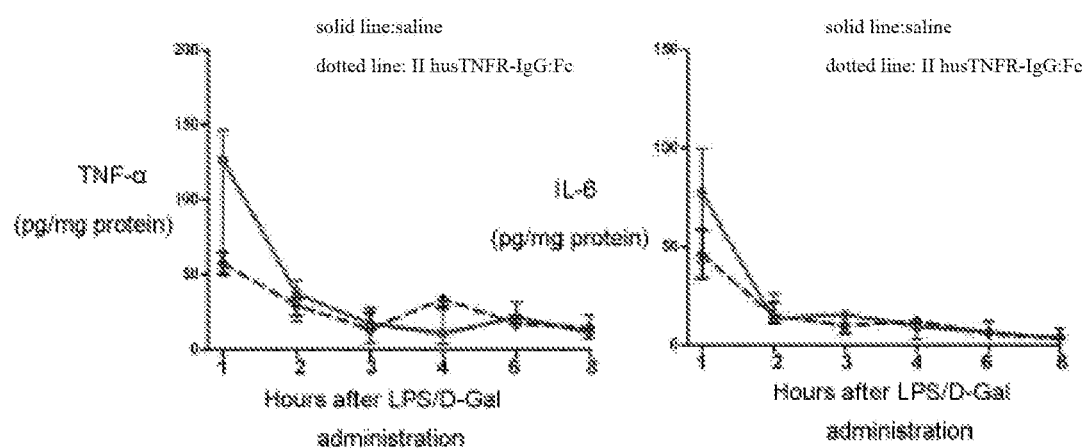

The pathological TUNEL staining results showed that there were 40-60 apoptotic bodies/high power field under a microscope in the control group, which was significantly more than those in the long-acting type II receptor subcutaneous injection prevention group with 5-8 apoptotic bodies/high power field, p<0.01. The detection of caspase 3 in the liver showed that the caspase 3 activity in the prevention group was 3 to 4 times lower than that in the control group. The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group (FIG. 2).

The liver NF-κB levels in the prevention group decreased by 30-50% compared to that in the control group, whereas the expression levels of the IL-22 and IL-22 receptors in the liver tissues increased by 2- to 5-fold. The above results indicated that the long-acting type II receptor subcutaneous injection prevention group 1) reduced massive hepatocyte necrosis through the inhibition of hepatic parenchymal cell apoptosis, 2) promoted hepatocyte survival and regeneration, and 3) inhibited SIRS in liver failure animals at the early stage of chronic liver disease with severe liver injury, thus greatly reducing the mortality rate.

Embodiment 5

Experiments of the Prevention of Chronic Liver Disease with Severe Liver Injury in Rats Using an Intravenous Injection of Long-Acting Recombinant Type II TNFα Receptor (Type II LHusTNFR), Indicated as Type II HusTNFR-IgG1:Fc The intravenous injection of type II LHusTNFR (the type II LHusTNFR-IgG1:Fc prepared in method (2) is the preventative drug) into the above four types of chronic liver disease with severe liver injury models was evaluated before the acute challenge of D-GaIN/LPS at a dose of 5-50 mg/kg. In one preferred embodiment, the dose used in the invention was 12.5 mg/kg. This treatment group was named the long-acting type II receptor intravenous injection prevention group. The injection of the long-acting type II soluble receptor type II LHusTNFR-IgG1:Fc is not limited to a specific time before the acute challenge of D-GaIN/LPS as long as the administration of drugs occurs before the acute challenge of D-GaIN/LPS. The preferred time is 0 to 36 hours before the acute challenge of D-GaIN/LPS. In addition, conventional HusTNFR intravenous injection rats are prepared at a dose of 12.5 mg/kg, which is the conventional type II receptor prevention group. The control group was the same species of rats with a intravenous injection of an equal volume of normal saline. In the rats with immune liver fibrosis induced by heterologous albumin, liver cirrhosis induced by carbon tetrachloride, alcoholic liver disease induced by ethanol, and non-alcoholic liver disease induced by a high-fat diet, the mortality rate of rats in the long-acting type II TNFα receptor intravenous injection group 24 hours after the D-GaIN/LPS injection was 0, whereas the mortality rate in the conventional type II TNFα receptor prevention group was 66%. The mortality rate of the chronic liver disease with severe liver injury model control group that did not receive long-acting or conventional type II TNFα treatment (abbreviated as the "control group") was 90%. Gross pathology showed that the original features of chronic liver injury, liver fibrosis, and liver cirrhosis in the liver of the long-acting type II receptor prevention group were still retained; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group (p<0.01). Using model 1 as an example, the liver injury scores are shown in FIG. 1. The left column is the liver with chronic liver fibrosis, the middle column is the long-acting type II receptor subcutaneous injection prevention group, and the right column is the control group.

The pathological TUNEL staining results showed that there were 40-60 apoptotic bodies/high power field under a microscope in the control group, which was significantly more than those in the long-acting type II receptor intravenous injection prevention group with 5-8 apoptotic bodies/high power field, p<0.01. The detection of caspase 3 in the liver showed that the caspase 3 activity in the prevention group was 3 to 4 times lower than that in the control group. The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group (FIG. 2).

The liver NF-κB levels in the prevention group decreased by 30-50% compared to that in the control group, whereas the expression levels of the IL-22 and IL-22 receptors in the liver tissues increased by 2- to 5-fold. The above results indicated that the long-acting type II receptor intravenous injection prevention group 1) reduced massive hepatocyte necrosis through the inhibition of hepatic parenchymal cell apoptosis, 2) promoted hepatocyte survival and regeneration, and 3) inhibited SIRS in liver failure animals at the early stage of chronic liver disease with severe liver injury, thus greatly reducing the mortality rate Embodiment 6

Experiments of the Treatment of Early-Stage Chronic Liver Disease with Severe Liver Injury in Rats Using a Subcutaneous Injection of Long-Acting Recombinant Type II TNFα Receptor (Type II LHusTNFR), Indicated as Type II HusTNFR-IgG1:Fc The subcutaneous injection of type II LHusTNFR (the type II LHusTNFR-IgG1:Fc prepared in method 2) at a dose of 5-50 mg/kg was treated into the above four types of chronic liver disease (presented in embodiment 1) or multiple ConA stimulations induced CARS model (presented in embodiment 2) after 0, 30 minutes, 1 hour, 1.5 hour for the acute challenge of D-GaIN/LPS. In one preferred embodiment, the dose used in the invention was 12.5 mg/kg.

The 2nd, 3rd, 4th, 6th and 8th hour's mortality after D-GaIN/LPS attacking for all four types of chronic liver disease (presented in embodiment 1) animals was 50%, 90%, 90% and 90% separately. However, the mortality of all four groups which treated by type II LHusTNFR-IgG1:Fc was 0. The control group was the same species of animals with a subcutaneous injection of an equal volume of normal saline. Mortality of the control group was 90% at the 2nd hour. There was no significant difference of 24 hour mortality rate between type II LHusTNFR-IgG1:Fc and normal saline treating CARS group at different time point by subcutaneous injection (0, ½, 1, 1.5, 2, 3, 4, 6 and 8 hours after D-GaIN/LPS attacking). the 24 hour mortality rate of both group was 15-20%. These data showed type II LHusTNFR-IgG1:Fc can effectively reducing the mortality rate when was treated animal at the early stage of chronic liver disease with severe liver injury.

Gross pathology showed that the original features of chronic liver injury, liver fibrosis, and liver cirrhosis in the liver were still retained for the long-acting type II receptor treating group at 0, 30 min, 1 hour, 1.5 hour after D-GaIN/LPS attacking; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group (p<0.01).

The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group. The liver NF-κB levels in the treating group decreased by 30-50% compared to that in the control group, whereas the expression levels of the IL-22 and IL-22 receptors in the liver tissues increased by 2- to 5-fold.

For type II LHusTNFR-IgG1:Fc treating animals at the time point at 3, 4, 6 and 8 hours after D-GaIN/LPS attacking, gross pathology showed there were massive or submissive of hepatic necrosis in the liver. There was no different for the liver injury score between type II LHusTNFR-IgG1:Fc treating and the control group.

Those above results indicated that type II LHusTNFR-IgG1:Fc subcutaneous injection could decrease the mortality for the early stage of chronic liver disease with severe hepatic injury through the following mechanisms: 1) reduced massive hepatocyte necrosis through the inhibition of hepatic parenchymal cell apoptosis, 2) promoted hepatocyte survival and regeneration, and 3) inhibited SIRS in liver failure animals at the early stage of chronic liver disease with severe liver injury, thus greatly reducing the mortality rate. However, type II LHusTNFR-IgG1:Fc could not improve the survival rate for advanced stage of the disease.

Embodiment 7

Experiments of the Treatment of Early-Stage Chronic Liver Disease with Severe Liver Injury in Rats Using an Intravenous Injection of Long-Acting Recombinant Type II TNFα Receptor (Type II LHusTNFR), Indicated as Type II HusTNFR-IgG:Fc The intravenous injection of type II LHusTNFR (the type II LHusTNFR-IgG1:Fc prepared in method 2) at a dose of 5-50 mg/kg was treated into the above four types of chronic liver disease (presented in embodiment 1) or multiple ConA stimulations induced CARS model (presented in embodiment 2) after 0, 30 minutes, 1 hour, 1.5 hour for the acute challenge of D-GaIN/LPS. In one preferred embodiment, the dose used in the invention was 12.5 mg/kg.

The 2nd, 3rd, 4th, 6th and 8th hour's mortality after D-GaIN/LPS attacking for all four types of chronic liver disease (presented in embodiment 1) animals was 50%, 90%, 90% and 90% separately. However, the mortality of all four groups which treated by type II LHusTNFR-IgG1:Fc was 0. The control group was the same species of animals with a intravenous injection of an equal volume of normal saline. Mortality of the control group was 90% at the 2nd hour. There was no significant difference of 24 hour mortality rate between type II LHusTNFR-IgG1:Fc and normal saline treating CARS group at different time point by intravenous injection (0, ½, 1, 1.5, 2, 3, 4, 6 and 8 hours after D-GaIN/LPS attacking). The 24 hour mortality rate of both group was 15-20%. These data showed type II LHusTNFR-IgG1:Fc can effectively reducing the mortality rate when was treated animal at the early stage of chronic liver disease with severe liver injury.

Gross pathology showed that the original features of chronic liver injury, liver fibrosis, and liver cirrhosis in the liver were still retained for the long-acting type II receptor treating group at 0, 30 min, 1 hour, 1.5 hour after D-GaIN/LPS attacking; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group ($p<0.01$).

The peak values of the peripheral plasma pro-inflammatory cytokines TNF$\alpha$ and IL-6 and the anti-inflammatory cytokine IL-10 significantly decreased compared to that in the chronic liver disease with severe liver injury control group. The peak values of liver TNF$\alpha$ and IL-6 significantly decreased compared to those in the chronic liver disease with severe liver injury control group. The liver NF-$\kappa$B levels in the treating group decreased by 30-50% compared to that in the control group, whereas the expression levels of the IL-22 and IL-22 receptors in the liver tissues increased by 2- to 5-fold.

For type II LHusTNFR-IgG1:Fc treating animals at the time point at 3, 4, 6 and 8 hours after D-GaIN/LPS attacking, gross pathology showed there were massive or submassive of hepatic necrosis in the liver. There was no different for the liver injury score between type II LHusTNFR-IgG1:Fc treating and the control group.

Those above results indicated that type II LHusTNFR-IgG1:Fc intravenous injection could decrease the mortality for the early stage of chronic liver disease with severe hepatic injury through the following mechanisms: 1) reduced massive hepatocyte necrosis through the inhibition of hepatic parenchymal cell apoptosis, 2) promoted hepatocyte survival and regeneration, and 3) inhibited SIRS in liver failure animals at the early stage of chronic liver disease with severe liver injury, thus greatly reducing the mortality rate. However, type II LHusTNFR-IgG1:Fc could not improve the survival rate for advanced stage of the disease.

Embodiment 8

Experiments of the Prevention of Chronic Liver Disease with Severe Liver Injury in Rats Using a Subcutaneous Injection of the Long-Acting Human Recombinant Soluble Type ITNF$\alpha$ Receptor (Type ILHusTNFR), Indicated as Type IHusTNFR-IgG1:Fc The subcutaneous injection of type I LHusTNFR (the type I LHusTNFR-IgG1:Fc prepared in method (2) is the preventative drug) into the above four types of chronic liver disease with severe liver injury models was evaluated before the acute challenge of D-GaIN/LPS at a dose of 5-50 mg/kg. In one preferred embodiment, the dose used in the invention was 12.5 mg/kg. This treatment group was named the long-acting type II receptor subcutaneous injection prevention group. The injection of the long-acting type II soluble receptor type I LHusTNFR-IgG1:Fc is not limited to a specific time before the acute challenge of D-GaIN/LPS as long as the administration of drugs occurs before the acute challenge of D-GaIN/LPS. The preferred time is 0 to 36 hours before the acute challenge of D-GaIN/LPS. In addition, conventional HusTNFR subcutaneous injection rats are prepared at a dose of 12.5 mg/kg, which is the conventional type I receptor prevention group. The control group was the same species of rats with a subcutaneous injection of an equal volume of normal saline. In the rats with immune liver fibrosis induced by heterologous albumin, liver cirrhosis induced by carbon tetrachloride, alcoholic liver disease induced by ethanol, and non-alcoholic liver disease induced by a high-fat diet, the mortality rate of rats in the long-acting type I TNF$\alpha$ receptor subcutaneous injection group 24 hours after the D-GaIN/LPS injection was 0, whereas the mortality rate in the conventional type I TNF$\alpha$ receptor prevention group was 66%. The mortality rate of the chronic liver disease with severe liver injury model control group that did not receive long-acting or conventional type I TNF$\alpha$ treatment (abbreviated as the "control group") was 90%. Gross pathology showed that the original features of chronic liver injury, liver fibrosis, and liver cirrhosis in the liver of the long-acting type I receptor prevention group were still retained; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group ($p<0.01$). Using model 1 as an example, the liver injury scores are shown in FIG. 1. The left column is the liver with chronic liver fibrosis, the middle column is the long-acting type II receptor subcutaneous injection prevention group, and the right column is the control group.

The pathological TUNEL staining results showed that there were 40-60 apoptotic bodies/high power field under a microscope in the control group, which was significantly more than those in the long-acting type I receptor subcutaneous injection prevention group with 5-8 apoptotic bodies/high power field, $p<0.01$. The detection of caspase 3 in the liver showed that the caspase 3 activity in the prevention group was 3 to 4 times lower than that in the control group. The peak values of the peripheral plasma pro-inflammatory cytokines TNF$\alpha$ and IL-6 and the anti-inflammatory cytokine IL-10 significantly decreased compared to that in the chronic liver disease with severe liver injury control group. The peak values of liver TNF$\alpha$ and IL-6 significantly decreased compared to those in the chronic liver disease with severe liver injury control group (FIG. 2).

The liver NF-$\kappa$B levels in the prevention group decreased by 30-50% compared to that in the control group, whereas the expression levels of the IL-22 and IL-22 receptors in the liver tissues increased by 2- to 5-fold. The above results indicated that the long-acting type I receptor subcutaneous injection prevention group 1) reduced massive hepatocyte necrosis through the inhibition of hepatic parenchymal cell apoptosis, 2) promoted hepatocyte survival and regeneration, and 3) inhibited SIRS in liver failure animals at the early stage of chronic liver disease with severe liver injury, thus greatly reducing the mortality rate.

Embodiment 9

Experiments of the Prevention of Chronic Liver Disease with Severe Liver Injury in Rats Using an Intravenous Injection of the Long-Acting Human Recombinant Soluble Type I TNFα Receptor (Type I LHusTNFR), Indicated as Type I HusTNFR-IgG1:Fc The intravenous injection of type I LHusTNFR (the type I LHusTNFR-IgG1:Fc prepared in method (2) is the preventative drug) into the above four types of chronic liver disease with severe liver injury models was evaluated before the acute challenge of D-GalN/LPS at a dose of 5-50 mg/kg. In one preferred embodiment, the dose used in the invention was 12.5 mg/kg. This treatment group was named the long-acting type II receptor intravenous injection prevention group. The injection of the long-acting type II soluble receptor type I LHusTNFR-IgG1:Fc is not limited to a specific time before the acute challenge of D-GalN/LPS as long as the administration of drugs occurs before the acute challenge of D-GalN/LPS. The preferred time is 0 to 36 hours before the acute challenge of D-GalN/LPS. In addition, conventional HusTNFR intravenous injection rats are prepared at a dose of 12.5 mg/kg, which is the conventional type I receptor prevention group. The control group was the same species of rats with a intravenous injection of an equal volume of normal saline. In the rats with immune liver fibrosis induced by heterologous albumin, liver cirrhosis induced by carbon tetrachloride, alcoholic liver disease induced by ethanol, and non-alcoholic liver disease induced by a high-fat diet, the mortality rate of rats in the long-acting type I TNFα receptor intravenous injection group 24 hours after the D-GalN/LPS injection was 0, whereas the mortality rate in the conventional type I TNFα receptor prevention group was 66%. The mortality rate of the chronic liver disease with severe liver injury model control group that did not receive long-acting or conventional type I TNFα treatment (abbreviated as the "control group") was 90%. Gross pathology showed that the original features of chronic liver injury, liver fibrosis, and liver cirrhosis in the liver of the long-acting type I receptor prevention group were still retained; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group ($p<0.01$). Using model 1 as an example, the liver injury scores are shown in FIG. 1. The left column is the liver with chronic liver fibrosis, the middle column is the long-acting type I receptor subcutaneous injection prevention group, and the right column is the control group.

The pathological TUNEL staining results showed that there were 40-60 apoptotic bodies/high power field under a microscope in the control group, which was significantly more than those in the long-acting type II receptor intravenous injection prevention group with 5-8 apoptotic bodies/high power field, $p<0.01$. The detection of caspase 3 in the liver showed that the caspase 3 activity in the prevention group was 3 to 4 times lower than that in the control group. The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group (FIG. 2).

The liver NF-κB levels in the prevention group decreased by 30-50% compared to that in the control group, whereas the expression levels of the IL-22 and IL-22 receptors in the liver tissues increased by 2- to 5-fold. The above results indicated that the long-acting type II receptor intravenous injection prevention group 1) reduced massive hepatocyte necrosis through the inhibition of hepatic parenchymal cell apoptosis, 2) promoted hepatocyte survival and regeneration, and 3) inhibited SIRS in liver failure animals at the early stage of chronic liver disease with severe liver injury, thus greatly reducing the mortality rate Embodiment 10

Experiments of the Treatment of Early-Stage Chronic Liver Disease with Severe Liver Injury in Rats Using a Subcutaneous Injection of the Long-Acting Human Recombinant Soluble Type I TNFα Receptor (Type I LHusTNFR), Indicated as Type I HusTNFR-IgG1:Fc The subcutaneous injection of type I LHusTNFR (the type I LHusTNFR-IgG1:Fc prepared in method 2) at a dose of 5-50 mg/kg was treated into the above four types of chronic liver disease (presented in embodiment 1) or multiple ConA stimulations induced CARS model (presented in embodiment 2) after 0, 30 minutes, 1 hour, 1.5 hour for the acute challenge of D-GalN/LPS. In one preferred embodiment, the dose used in the invention was 12.5 mg/kg.

The 2nd, 3rd, 4th, 6th and 8th hour's mortality after D-GalN/LPS attacking for all four types of chronic liver disease (presented in embodiment 1) animals was 50%, 90%, 90% and 90% separately. However, the mortality of all four groups which treated by type I LHusTNFR-IgG1:Fc was 0. The control group was the same species of animals with a subcutaneous injection of an equal volume of normal saline. Mortality of the control group was 90% at the 2nd hour. There was no significant difference of 24 hour mortality rate between type ILHusTNFR-IgG1:Fc and normal saline treating CARS group at different time point by subcutaneous injection (0, ½, 1, 1.5, 2, 3, 4, 6 and 8 hours after D-GalN/LPS attacking). the 24 hour mortality rate of both group was 15-20%. These data showed type I LHusTNFR-IgG1:Fc can effectively reducing the mortality rate when was treated animal at the early stage of chronic liver disease with severe liver injury.

Gross pathology showed that the original features of chronic liver injury, liver fibrosis, and liver cirrhosis in the liver were still retained for the long-acting type I receptor treating group at 0, 30 min, 1 hour, 1.5 hour after D-GalN/LPS attacking; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group ($p<0.01$).

The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group. The liver NF-κB levels in the treating group decreased by 30-50% compared to that in the control group, whereas the expression levels of the IL-22 and IL-22 receptors in the liver tissues increased by 2- to 5-fold.

For type I LHusTNFR-IgG1:Fc treating animals at the time point at 3, 4, 6 and 8 hours after D-GalN/LPS attacking, gross pathology showed there were massive or submissive of hepatic necrosis in the liver. There was no different for the liver injury score between type I LHusTNFR-IgG1:Fc treating and the control group.

Those above results indicated that type I LHusTNFR-IgG1:Fc subcutaneous injection could decrease the mortality for the early stage of chronic liver disease with severe hepatic injury through the following mechanisms: 1) reduced massive hepatocyte necrosis through the inhibition of hepatic parenchymal cell apoptosis, 2) promoted hepatocyte survival and regeneration, and 3) inhibited SIRS in liver failure animals at the early stage of chronic liver disease with severe liver injury, thus greatly reducing the mortality rate. However, type I LHusTNFR-IgG1:Fc could not improve the survival rate for advanced stage of the disease.

Embodiment 11

Experiments of the Treatment of Early-Stage Chronic Liver Disease with Severe Liver Injury in Rats Using an Intravenous Injection of the Long-Acting Human Recombinant Soluble Type I TNFα Receptor (Type I LHusTNFR), Indicated as Type I HusTNFR-IgG1:Fc The intravenous injection of type I LHusTNFR (the type I LHusTNFR-IgG1:Fc prepared in method 2) at a dose of 5-50 mg/kg was treated into the above four types of chronic liver disease (presented in embodiment 1) or multiple ConA stimulations induced CARS model (presented in embodiment 2) after 0, 30 minutes, 1 hour, 1.5 hour for the acute challenge of D-GaIN/LPS. In one preferred embodiment, the dose used in the invention was 12.5 mg/kg.

The 2nd, 3rd, 4th, 6th and 8th hour's mortality after D-GaIN/LPS attacking for all four types of chronic liver disease (presented in embodiment 1) animals was 50%, 90%, 90% and 90% separately. However, the mortality of all four groups which treated by type I LHusTNFR-IgG1:Fc was 0. The control group was the same species of animals with a intravenous injection of an equal volume of normal saline. Mortality of the control group was 90% at the 2nd hour. There was no significant difference of 24 hour mortality rate between type I LHusTNFR-IgG1:Fc and normal saline treating CARS group at different time point by intravenous injection (0, ½, 1, 1.5, 2, 3, 4, 6 and 8 hours after D-GaIN/LPS attacking). The 24 hour mortality rate of both group was 15-20%. These data showed type II LHusTNFR-IgG1:Fc can effectively reducing the mortality rate when was treated animal at the early stage of chronic liver disease with severe liver injury.

Gross pathology showed that the original features of chronic liver injury, liver fibrosis, and liver cirrhosis in the liver were still retained for the long-acting type I receptor treating group at 0, 30 min, 1 hour, 1.5 hour after D-GaIN/LPS attacking; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group ($p<0.01$).

The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group. The liver NF-κB levels in the treating group decreased by 30-50% compared to that in the control group, whereas the expression levels of the IL-22 and IL-22 receptors in the liver tissues increased by 2- to 5-fold.

For type I LHusTNFR-IgG1:Fc treating animals at the time point at 3, 4, 6 and 8 hours after D-GaIN/LPS attacking, gross pathology showed there were massive or submissive of hepatic necrosis in the liver. There was no different for the liver injury score between type I LHusTNFR-IgG1:Fc treating and the control group.

Those above results indicated that type I LHusTNFR-IgG1:Fc intravenous injection could decrease the mortality for the early stage of chronic liver disease with severe hepatic injury through the following mechanisms: 1) reduced massive hepatocyte necrosis through the inhibition of hepatic parenchymal cell apoptosis, 2) promoted hepatocyte survival and regeneration, and 3) inhibited SIRS in liver failure animals at the early stage of chronic liver disease with severe liver injury, thus greatly reducing the mortality rate. However, type I LHusTNFR-IgG1:Fc could not improve the survival rate for advanced stage of the disease.

Embodiment 12

Experiments of the Prevention and Treatment of Early-Stage Chronic Liver Disease with Severe Liver Injury Using an Intravenous Injection of the Product of the Connection Between the Amino Terminus of Human Type I Tumor Necrosis Factor α Receptor and PEG and the Product of the Connection Between the Carboxyl Terminus of Human Type I Tumor Necrosis Factor α Receptor and PEG Both the product of the connection between the amino terminus of human type I tumor necrosis factor α receptor and PEG and the product of the connection between the carboxyl terminus of human type I tumor necrosis factor α receptor and PEG was made as a conventional methods (Methods 3). Tail vein injecting of type I LHusTNFR-PEG at a dose of 5-50 mg/kg into the above four types of chronic liver disease (presented in embodiment 1) at a dose of 5-50 mg/kg was evaluated before the acute challenge of D-GaIN/LPS. In one preferred embodiment, the dose used in the invention was 12.5 mg/kg. This treatment group was named the long-acting type I receptor intravenous injection prevention group.

The injection of type I LHusTNFR-PEG is not limited to a specific time before the acute challenge of D-GaIN/LPS as long as the administration of drugs occurs before the acute challenge of D-GaIN/LPS. The preferred time is 0 to 36 hours before the acute challenge of D-GaIN/LPS. In one preferred embodiment, the time point used in the invention was 2 hours before D-GaIN/LPS challenge. In addition, conventional HusTNFR subcutaneous injection rats are prepared at a dose of 12.5 mg/kg, which is the conventional type I receptor prevention group. The control group was the same species of rats with a subcutaneous injection of an equal volume of normal saline.

In the rats with immune liver fibrosis induced by heterologous albumin, liver cirrhosis induced by carbon tetrachloride, alcoholic liver disease induced by ethanol, and non-alcoholic liver disease induced by a high-fat diet, the mortality rate of rats in the long-acting type I TNFα receptor intravenous injection group 24 hours after the D-GaIN/LPS injection was 0, whereas the mortality rate in the conventional type I TNFα receptor prevention group was 60%. The mortality rate of the control group was 90%. Gross pathology showed that the original features of chronic liver injury, liver fibrosis, and liver cirrhosis in the liver of the long-acting type I receptor prevention group were still retained; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group ($p<0.01$).

The pathological TUNEL staining results showed that there were 40-60 apoptotic bodies/high power field under a microscope in the control group, which was significantly more than those in the long-acting type I receptor intravenous injection prevention group with 5-8 apoptotic bodies/high power field, $p<0.001$. The detection of caspase 3 in the liver showed that the caspase 3 activity in the prevention group was 3 to 4 times lower than that in the control group. The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group. The liver NF-κB levels in the prevention group decreased by 30-50% compared to that in the control group, whereas the expression levels of the IL-22 and IL-22 receptors in the liver tissues increased by 2- to 5-fold.

The tail intravenous injection of type I LHusTNFR-PEG into above four types of chronic liver disease (presented in embodiment 1) was evaluated after 0.5, 1, 2, 3, 4, 6 or 8 hour after the acute challenge of D-GaIN/LPS. The mortality rate of type I LHusTNFR-PEG injecting at time point at 0.5, 1, 2 hours after D-GaIN/LPS challenging was 0, however The mortality rate raised to 80-90% for type I LHusTNFR-PEG injecting at time point later than 4 hours after D-GaIN/LPS challenging. Those results showed both of two different linked form of type I LHusTNFR-PEG can effectively improve the mortality rate for early stage of chronic liver disease with severe liver injury.

Embodiment 13

Experiments of the Prevention and Treatment of Early-Stage Chronic Liver Disease with Severe Liver Injury Using an Intravenous Injection of the Product of the Connection Between the Amino Terminus of Human Type II Tumor Necrosis Factor α Receptor and PEG and the Product of the Connection Between the Carboxyl Terminus of Human Type II Tumor Necrosis Factor α Receptor and PEG Both the product of the connection between the amino terminus of human type II tumor necrosis factor α receptor and PEG and the product of the connection between the carboxyl terminus of human type II tumor necrosis factor α receptor and PEG was made as a conventional methods. Tail vein injecting of type II LHusTNFR-PEG at a dose of 5-50 mg/kg into the above four types of chronic liver disease (presented in embodiment 1) at a dose of 5-50 mg/kg was evaluated before the acute challenge of D-GaIN/LPS. In one preferred embodiment, the dose used in the invention was 12.5 mg/kg. This treatment group was named the long-acting type II receptor intravenous injection prevention group.

The injection of type II LHusTNFR-PEG is not limited to a specific time before the acute challenge of D-GaIN/LPS as long as the administration of drugs occurs before the acute challenge of D-GaIN/LPS. The preferred time is 0 to 36 hours before the acute challenge of D-GaIN/LPS. In one preferred embodiment, the time point used in the invention was 2 hours before D-GaIN/LPS challenge. In addition, conventional HusTNFR subcutaneous injection rats are prepared at a dose of 12.5 mg/kg, which is the conventional type II receptor prevention group. The control group was the same species of rats with a subcutaneous injection of an equal volume of normal saline.

In the rats with immune liver fibrosis induced by heterologous albumin, liver cirrhosis induced by carbon tetrachloride, alcoholic liver disease induced by ethanol, and non-alcoholic liver disease induced by a high-fat diet, the mortality rate of rats in the long-acting type II TNFα receptor intravenous injection group 24 hours after the D-GaIN/LPS injection was 0, whereas the mortality rate in the conventional type II TNFα receptor prevention group was 60%. The mortality rate of the control group was 90%. Gross pathology showed that the original features of chronic liver injury, liver fibrosis, and liver cirrhosis in the liver of the long-acting type II receptor prevention group were still retained; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group ($p<0.01$).

The pathological TUNEL staining results showed that there were 40-60 apoptotic bodies/high power field under a microscope in the control group, which was significantly more than those in the long-acting type I receptor intravenous injection prevention group with 5-8 apoptotic bodies/high power field, $p<0.001$. The detection of caspase 3 in the liver showed that the caspase 3 activity in the prevention group was 3 to 4 times lower than that in the control group. The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group. The liver NF-κB levels in the prevention group decreased by 30-50% compared to that in the control group, whereas the expression levels of the IL-22 and IL-22 receptors in the liver tissues increased by 2- to 5-fold.

The tail intravenous injection of type II LHusTNFR-PEG into above four types of chronic liver disease (presented in embodiment 1) was evaluated after 0.5, 1, 2, 3, 4, 6 or 8 hour after the acute challenge of D-GaIN/LPS. The mortality rate of type II LHusTNFR-PEG injecting at time point at 0.5, 1, 2 hours after D-GaIN/LPS challenging was 0, however The mortality rate raised to 80-90% for type II LHusTNFR-PEG injecting at time point later than 4 hours after D-GaIN/LPS challenging. Those results showed both of two different linked form of type II LHusTNFR-PEG can effectively improve the mortality rate for early stage of chronic liver disease with severe liver injury.

Embodiment 14

Experiments of the Prevention of Chronic Liver Disease with Severe Liver Injury in Rats and the Treatment of Early-Stage Chronic Liver Disease with Severe Liver Injury in Rats Using an Intravenous Injection of Human Type I Tumor Necrosis Factor α Embedded in PEG-Liposomes human type I tumor necrosis factor α embedded in PEG-liposomes was made as a conventional methods (Methods 5). Tail vein injecting of type I LHusTNFR-PEG-liposomes at a dose of 5-50 mg/kg into the above four types of chronic liver disease (presented in embodiment 1) at a dose of 5-50 mg/kg was evaluated before the acute challenge of D-GaIN/LPS. In one preferred embodiment, the dose used in the invention was 12.5 mg/kg. This treatment group was named the long-acting type I receptor intravenous injection prevention group.

The injection of type I LHusTNFR-PEG-liposomes is not limited to a specific time before the acute challenge of D-GaIN/LPS as long as the administration of drugs occurs before the acute challenge of D-GaIN/LPS. The preferred time is 0 to 36 hours before the acute challenge of D-GaIN/LPS. In one preferred embodiment, the time point used in the invention was 2 hours before D-GaIN/LPS challenge. In addition, conventional HusTNFR subcutaneous injection rats are prepared at a dose of 12.5 mg/kg, which is the conventional type I receptor prevention group. The control group was the same species of rats with a subcutaneous injection of an equal volume of normal saline.

In the rats with immune liver fibrosis induced by heterologous albumin, liver cirrhosis induced by carbon tetrachloride, alcoholic liver disease induced by ethanol, and non-alcoholic liver disease induced by a high-fat diet, the mortality rate of rats in the long-acting type I TNFα receptor intravenous injection group 24 hours after the D-GaIN/LPS injection was 0, whereas the mortality rate in the conventional type I TNFα receptor prevention group was 60%. The mortality rate of the control group was 90%. Gross pathology showed that the original features of chronic liver injury, liver fibrosis, and liver cirrhosis in the liver of the long-acting type I receptor prevention group were still retained; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group (p<0.01).

The pathological TUNEL staining results showed that there were 40-60 apoptotic bodies/high power field under a microscope in the control group, which was significantly more than those in the long-acting type I receptor intravenous injection prevention group with 5-8 apoptotic bodies/high power field, p<0.001. The detection of caspase 3 in the liver showed that the caspase 3 activity in the prevention group was 3 to 4 times lower than that in the control group. The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group. The liver NF-κB levels in the prevention group decreased by 30-50% compared to that in the control group, whereas the expression levels of the IL-22 and IL-22 receptors in the liver tissues increased by 2- to 5-fold.

The tail intravenous injection of type I LHusTNFR-PEG-liposomes into above four types of chronic liver disease (presented in embodiment 1) after 0.5, 1, 2, 3, 4, 6 or 8 hour after the acute challenge of D-GaIN/LPS. The mortality rate of type I LHusTNFR-PEG-liposomes injecting at time point at 0.5, 1, 2 hours after D-GaIN/LPS challenging was 0, however The mortality rate raised to 80-90% for type I LHusTNFR-PEG-liposomes injecting at time point later than 4 hours after D-GaIN/LPS challenging. Those results showed both of two different linked form of type I LHusTNFR-PEG-liposomes can effectively improve the mortality rate for early stage of chronic liver disease with severe liver injury.

Embodiment 15

Experiments of the Prevention of Chronic Liver Disease with Severe Liver Injury in Rats and the Treatment of Early-Stage Chronic Liver Disease with Severe Liver Injury in Rats Using an Intravenous Injection of Human Type II Tumor Necrosis Factor α Embedded in PEG-Liposomes human type II tumor necrosis factor α embedded in PEG-liposomes was made as a conventional methods (Methods 5). Tail vein injecting of type II LHusTNFR-PEG-liposomes at a dose of 5-50 mg/kg into the above four types of chronic liver disease (presented in embodiment 1) at a dose of 5-50 mg/kg was evaluated before the acute challenge of D-GaIN/LPS. In one preferred embodiment, the dose used in the invention was 12.5 mg/kg. This treatment group was named the long-acting type II receptor intravenous injection prevention group.

The injection of type II LHusTNFR-PEG-liposomes is not limited to a specific time before the acute challenge of D-GaIN/LPS as long as the administration of drugs occurs before the acute challenge of D-GaIN/LPS. The preferred time is 0 to 36 hours before the acute challenge of D-GaIN/LPS. In one preferred embodiment, the time point used in the invention was 2 hours before D-GaIN/LPS challenge. In addition, conventional HusTNFR subcutaneous injection rats are prepared at a dose of 12.5 mg/kg, which is the conventional type II receptor prevention group. The control group was the same species of rats with a subcutaneous injection of an equal volume of normal saline.

In the rats with immune liver fibrosis induced by heterologous albumin, liver cirrhosis induced by carbon tetrachloride, alcoholic liver disease induced by ethanol, and non-alcoholic liver disease induced by a high-fat diet, the mortality rate of rats in the long-acting type II TNFα receptor intravenous injection group 24 hours after the D-GaIN/LPS injection was 0, whereas the mortality rate in the conventional type II TNFα receptor prevention group was 60%. The mortality rate of the control group was 90%. Gross pathology showed that the original features of chronic liver injury, liver fibrosis, and liver cirrhosis in the liver of the long-acting type II receptor prevention group were still retained; however, liver parenchyma only displays mild congestion and swelling, a small amount of focal necrosis, and no massive or submassive necrosis. The liver injury score (based on the severity of the lesion, the importance of the lesion, and the area of injured liver tissues observed in HE staining of rat liver tissue sections; semi-quantitative scoring is conducted) was 2±1 points, which was significantly less than the 5±2 points in the control group (p<0.01).

The pathological TUNEL staining results showed that there were 40-60 apoptotic bodies/high power field under a microscope in the control group, which was significantly more than those in the long-acting type II receptor intravenous injection prevention group with 5-8 apoptotic bodies/high power field, p<0.001. The detection of caspase 3 in the liver showed that the caspase 3 activity in the prevention group was 3 to 4 times lower than that in the control group.

The peak values of the peripheral plasma pro-inflammatory cytokines TNFα and IL-6 and the anti-inflammatory cytokine IL-10 significantly decreased compared to that in the chronic liver disease with severe liver injury control group. The peak values of liver TNFα and IL-6 significantly decreased compared to those in the chronic liver disease with severe liver injury control group. The liver NF-κB levels in the prevention group decreased by 30-50% compared to that in the control group, whereas the expression levels of the IL-22 and IL-22 receptors in the liver tissues increased by 2- to 5-fold.

The tail intravenous injection of type II LHusTNFR-PEG-liposomes into above four types of chronic liver disease (presented in embodiment 1) after 0.5, 1, 2, 3, 4, 6 or 8 hour after the acute challenge of D-GaIN/LPS. The mortality rate of type II LHusTNFR-PEG-liposomes injecting at time point at 0.5, 1, 2 hours after D-GaIN/LPS challenging was 0, however The mortality rate raised to 80-90% for type II LHusTNFR-PEG-liposomes injecting at time point later than 4 hours after D-GaIN/LPS challenging. Those results showed both of two different linked form of type II LHus-TNFR-PEG-liposomes can effectively improve the mortality rate for early stage of chronic liver disease with severe liver injury.

All the literature studies mentioned in this invention are cited in this application for reference, and each study is cited alone for reference. In addition, it should be understood that after reading the above content of this invention, technical experts in this field can perform various amendments or modifications of this invention; these equivalents also fall into the scope of claims in the present application.

The invention claimed is:

1. A method for decreasing mortality associated with chronic liver disease with severe liver injury or hepatic necrosis caused by chronic liver disease comprising:
administering a therapeutically effective amount of long-acting human recombinant soluble tumor necrosis factor α receptor (LHusTNFR) to a patient having a chronic liver disease,
wherein the chronic liver disease includes liver fibrosis, liver cirrhosis, or liver disease induced by a high-fat diet, or a combination thereof.

2. A method for decreasing mortality associated with chronic liver disease comprising:
administering a therapeutically effective amount of long-acting human recombinant soluble tumor necrosis factor α receptor (LHusTNFR) to a patient whose condition is early-stage chronic liver disease with severe liver injury or early-stage hepatic necrosis caused by chronic liver disease,
wherein the chronic liver disease includes liver fibrosis, liver cirrhosis, alcoholic liver disease, or liver disease induced by a high-fat diet, or a combination thereof.

3. The method of claim 1, wherein the LHusTNFR is selected from the following group:
a. a fusion protein between human type I tumor necrosis factor α receptor and the human IgG1:Fc fragment,
b. a fusion protein between human type II tumor necrosis factor α receptor and the human IgG1:Fc fragment,
c. a conjugated product between the amino terminus of human type I tumor necrosis factor α receptor and polyethylene glycol (PEG),
d. a conjugated product between the carboxyl terminus of human type I tumor necrosis factor α receptor and PEG,
e. a conjugated protein between the amino terminus of human type II tumor necrosis factor α receptor and PEG,
f. a conjugated product between the carboxyl terminus of human type II tumor necrosis factor α receptor and PEG,
g. a human type I tumor necrosis factor α receptor protein product embedded in a PEG-liposome mixture, and
h. a human type II tumor necrosis factor α receptor protein product embedded in a PEG-liposome mixture.

4. The method of claim 2, wherein the LHusTNFR is selected from the following group:
a. a fusion protein between human type I tumor necrosis factor α receptor and the human IgG1:Fc fragment,
b. a fusion protein between human type II tumor necrosis factor α receptor and the human IgG1:Fc fragment,
c. a conjugated product between the amino terminus of human type I tumor necrosis factor α receptor and PEG,
d. a conjugated product between the carboxyl terminus of human type I tumor necrosis factor α receptor and PEG,
e. a conjugated protein between the amino terminus of human type II tumor necrosis factor α receptor and PEG,
f. a conjugated product between the carboxyl terminus of human type II tumor necrosis factor α receptor and PEG,
g. a human type I tumor necrosis factor α receptor protein product embedded in a PEG-liposome mixture, and
h. a human type II tumor necrosis factor α receptor protein product embedded in a PEG-liposome mixture.

\* \* \* \* \*

SEQUENCE LISTING

```
<160> NUMBER OF SEQ ID NOS: 4

<210> SEQ ID NO 1
<211> LENGTH: 403
<212> TYPE: PRT
<213> ORGANISM: Homo sapiens
<220> FEATURE:
<221> NAME/KEY: MISC_FEATURE
<223> OTHER INFORMATION: fusion protein

<400> SEQUENCE: 1

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
                85                  90                  95

Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
        115                 120                 125

His Ala Gly Phe Phe Leu Arg Glu Asn Glu Cys Val Ser Cys Ser Asn
    130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr Glu Pro Lys Ser Cys
                165                 170                 175

Asp Lys Thr His Thr Cys Pro Pro Cys Pro Ala Pro Glu Leu Leu Gly
            180                 185                 190

Gly Pro Ser Val Phe Leu Phe Pro Pro Lys Pro Lys Asp Thr Leu Met
        195                 200                 205

Ile Ser Arg Thr Pro Glu Val Thr Cys Val Val Val Asp Val Ser His
    210                 215                 220

Glu Asp Pro Glu Val Lys Phe Asn Trp Tyr Val Asp Gly Val Glu Val
225                 230                 235                 240
```

His Asn Ala Lys Thr Lys Pro Arg Glu Glu Gln Tyr Asn Ser Thr Tyr
                245                 250                 255

Arg Val Val Ser Val Leu Thr Val Leu His Gln Asp Trp Leu Asn Gly
            260                 265                 270

Lys Glu Tyr Lys Cys Lys Val Ser Asn Leu Ala Leu Pro Ala Pro Ile
        275                 280                 285

Glu Lys Thr Ile Ser Lys Ala Lys Gly Gln Pro Arg Glu Pro Gln Val
    290                 295                 300

Tyr Thr Leu Pro Pro Ser Arg Glu Glu Met Thr Lys Asn Gln Val Ser
305                 310                 315                 320

Leu Thr Cys Leu Val Lys Gly Phe Tyr Pro Ser Asp Ile Ala Val Glu
                325                 330                 335

Trp Glu Ser Asn Gly Gln Pro Glu Asn Asn Tyr Lys Thr Thr Pro Pro
            340                 345                 350

Val Leu Asp Ser Asp Gly Ser Phe Phe Leu Tyr Ser Lys Leu Thr Val
        355                 360                 365

Asp Lys Ser Arg Trp Gln Gln Gly Asn Val Phe Ser Cys Ser Val Met
    370                 375                 380

His Glu Ala Leu His Asn His Tyr Thr Gln Lys Ser Leu Ser Leu Ser
385                 390                 395                 400

Pro Gly Lys

<210> SEQ ID NO 2
<211> LENGTH: 467
<212> TYPE: PRT
<213> ORGANISM: artificial sequence
<220> FEATURE:
<221> NAME/KEY: MISC_FEATURE
<223> OTHER INFORMATION: fusion protein

<400> SEQUENCE: 2

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
                165                 170                 175

Val Cys Thr Ser Thr Ser Pro Thr Arg Ser Met Ala Pro Gly Ala Val
            180                 185                 190

```
His Leu Pro Gln Pro Val Ser Thr Arg Ser Gln His Thr Gln Pro Thr
        195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Leu Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Glu Glu Met Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445

His Glu Ala Leu His Asn His Tyr Thr Gln Lys Ser Leu Ser Leu Ser
    450                 455                 460

Pro Gly Lys
465

<210> SEQ ID NO 3
<211> LENGTH: 171
<212> TYPE: PRT
<213> ORGANISM: Homo sapiens

<400> SEQUENCE: 3

Asp Ser Val Cys Pro Gln Gly Lys Tyr Ile His Pro Gln Asn Asn Ser
1               5                   10                  15

Ile Cys Cys Thr Lys Cys His Lys Gly Thr Tyr Leu Tyr Asn Asp Cys
            20                  25                  30

Pro Gly Pro Gly Gln Asp Thr Asp Cys Arg Glu Cys Glu Ser Gly Ser
        35                  40                  45

Phe Thr Ala Ser Glu Asn His Leu Arg His Cys Leu Ser Cys Ser Lys
    50                  55                  60

Cys Arg Lys Glu Met Gly Gln Val Glu Ile Ser Ser Cys Thr Val Asp
65                  70                  75                  80

Arg Asp Thr Val Cys Gly Cys Arg Lys Asn Gln Tyr Arg His Tyr Trp
            85                  90                  95
```

```
Ser Glu Asn Leu Phe Gln Cys Phe Asn Cys Ser Leu Cys Leu Asn Gly
            100                 105                 110

Thr Val His Leu Ser Cys Gln Glu Lys Gln Asn Thr Val Cys Thr Cys
            115                 120                 125

His Ala Gly Phe Phe Leu Arg Glu Asn Glu Cys Val Ser Cys Ser Asn
        130                 135                 140

Cys Lys Lys Ser Leu Glu Cys Thr Lys Leu Cys Leu Pro Gln Ile Glu
145                 150                 155                 160

Asn Val Lys Gly Thr Glu Asp Ser Gly Thr Thr
                165                 170

<210> SEQ ID NO 4
<211> LENGTH: 235
<212> TYPE: PRT
<213> ORGANISM: Homo sapiens

<400> SEQUENCE: 4

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
            85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
130                 135                 140

Gly Thr Phe Ser Asn Thr Thr Ser Ser Thr Asp Ile Cys Arg Pro His
145                 150                 155                 160

Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
        180                 185                 190

His Leu Pro Gln Pro Val Ser Thr Arg Ser Gln His Thr Gln Pro Thr
    195                 200                 205

Pro Glu Pro Ser Thr Ala Pro Ser Thr Ser Phe Leu Leu Pro Met Gly
    210                 215                 220

Pro Ser Pro Pro Ala Glu Gly Ser Thr Gly Asp
225                 230                 235
```